US011589767B2

(12) United States Patent
Valvano et al.

(10) Patent No.: US 11,589,767 B2
(45) Date of Patent: *Feb. 28, 2023

(54) LOW POWER APPARATUS AND METHOD TO MEASURE COMPLEX ELECTRICAL ADMITTANCE OR IMPEDANCE

(71) Applicants: Jonathan W. Valvano, Austin, TX (US); Marc D. Feldman, San Antonio, TX (US); John Porterfield, Austin, TX (US); John A. Pearce, Austin, TX (US); Erik Larson, Austin, TX (US); Lev Shuhatovich, Houston, TX (US); Kathryn Loeffler, Leander, TX (US); Raffaele Cetrulo, Houston, TX (US)

(72) Inventors: Jonathan W. Valvano, Austin, TX (US); Marc D. Feldman, San Antonio, TX (US); John Porterfield, Austin, TX (US); John A. Pearce, Austin, TX (US); Erik Larson, Austin, TX (US); Lev Shuhatovich, Houston, TX (US); Kathryn Loeffler, Leander, TX (US); Raffaele Cetrulo, Houston, TX (US)

(73) Assignees: Board of Regents, The University of Texas System, Austin, TX (US); Admittance Technologies, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/536,146

(22) Filed: Aug. 8, 2019

(65) Prior Publication Data

US 2019/0357805 A1 Nov. 28, 2019

Related U.S. Application Data

(60) Division of application No. 15/044,842, filed on Feb. 16, 2016, now Pat. No. 10,376,177, which is a
(Continued)

(51) Int. Cl.
*A61B 5/0538* (2021.01)
*A61N 1/05* (2006.01)
(Continued)

(52) U.S. Cl.
CPC ............ *A61B 5/0538* (2013.01); *A61B 5/029* (2013.01); *A61B 5/0215* (2013.01); *A61N 1/056* (2013.01);
(Continued)

(58) Field of Classification Search
CPC ................ A61N 1/365; A61N 1/36514; A61N 1/36521; A61N 1/36125
See application file for complete search history.

(56) References Cited

U.S. PATENT DOCUMENTS 5,280,429 A * 1/1994 Withers ............... A61B 5/0535
378/70
5,709,709 A * 1/1998 Kroll .................. A61N 1/36521
607/4
(Continued)

FOREIGN PATENT DOCUMENTS

JP S61-079308 A 9/1984
JP 2004-508149 A 3/2004
(Continued)

OTHER PUBLICATIONS

National Instruments, "Timing and Synchronization of Modular Measuring Equipment Using T-Clock Technology of National Instruments," Japan, Oct. 26, 2008.
(Continued)

*Primary Examiner* — Joseph M Dietrich
(74) *Attorney, Agent, or Firm* — Ansel M. Schwartz

(57) ABSTRACT

An apparatus for measuring complex electrical admittance and/or complex electrical impedance in animal or human patients includes a first electrode and at least a second
(Continued)

electrode which are adapted to be disposed in the patient. The apparatus includes a housing adapted to be disposed in the patient. The housing has disposed in it a stimulator in electrical communication with at least the first electrode to stimulate the first electrode with either current or voltage, a sensor in electrical communication with at least the second electrode to sense a response from the second electrode based on the stimulation of the first electrode, and a signal processor in electrical communication with the sensor to determine the complex electrical admittance or impedance of the patient.

6 Claims, 18 Drawing Sheets

Related U.S. Application Data continuation of application No. 13/425,119, filed on Mar. 20, 2012, now Pat. No. 9,295,404.

(60) Provisional application No. 61/516,138, filed on Mar. 30, 2011.

(51) Int. Cl.
*A61N 1/36* (2006.01)
*A61N 1/365* (2006.01)
*A61N 1/37* (2006.01)
*A61B 5/0215* (2006.01)
*A61B 5/029* (2006.01)

(52) U.S. Cl.
CPC ..... *A61N 1/36125* (2013.01); *A61N 1/36521* (2013.01); *A61N 1/3706* (2013.01)

(56) References Cited

U.S. PATENT DOCUMENTS

2010/0249756 A1* 9/2010 Koh ............... A61B 5/418
604/890.1
2010/0280397 A1 11/2010 Feldman et al.

FOREIGN PATENT DOCUMENTS

JP 2010-082362 A 10/2008
WO WO 02/22208 A2 9/2001

OTHER PUBLICATIONS

Agilent Technologies, Impedance Measurement Handbook, Japan Agilent Technologies, Oct. 31, 2003, 5950-3000JA.
Masayuki Hirai, Trial of Making Left Ventricular Pressure Volume Curve (P-V) In Clinical Case, Journal of Japanese Society of Radiological Technology, Japan, Japanese Society of Technology, Aug. 1987, vol. 43, No. 8, URL: http://ci.nii.ac.jp/naid/110003443718.

* cited by examiner

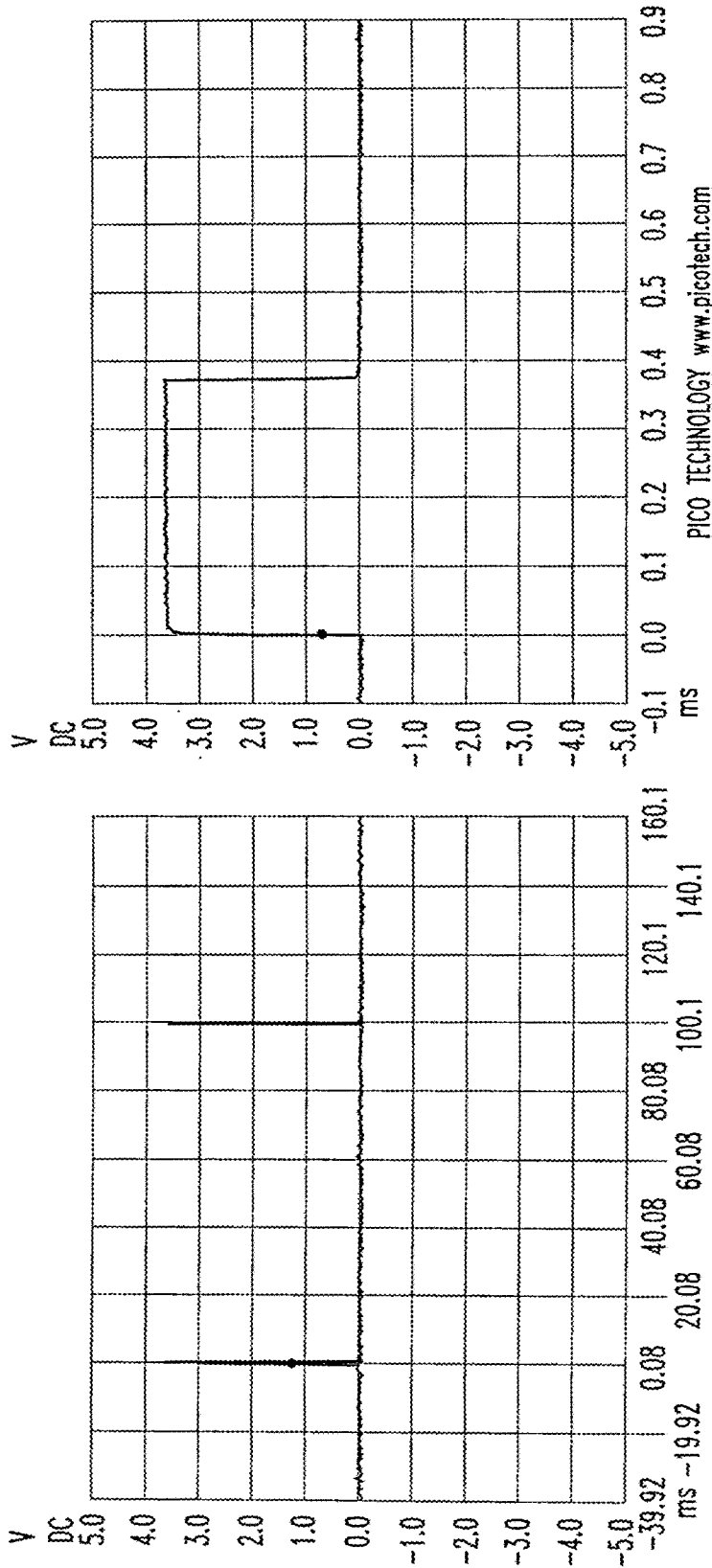

LOW POWER APPARATUS AND METHOD TO MEASURE COMPLEX ELECTRICAL ADMITTANCE OR IMPEDANCE

CROSS-REFERENCE TO RELATED APPLICATIONS

This is a divisional of U.S. patent application Ser. No. 15/044,842 filed Feb. 16, 2016, now U.S. Pat. No. 10,376,177, which is a continuation of U.S. patent application Ser. No. 13/425,119 filed Mar. 20, 2012, now U.S. Pat. No. 9,295,404 issued on Mar. 29, 2016, which claims the benefit of U.S. provisional patent application Ser. No. 61/516,138 filed Mar. 30, 2011, all of which are incorporated by reference herein.

FIELD OF THE INVENTION

The present invention is related to measuring complex electrical admittance and/or complex electrical impedance in animal or human patients using low power. (As used herein, references to the "present invention" or "invention" relate to exemplary embodiments and not necessarily to every embodiment encompassed by the appended claims.) More specifically, the present invention is related to measuring complex electrical admittance and/or complex electrical impedance in animal or human patients using low power where the low power that is used is less than an average current of less than 23 mA in operation over time.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Congestive heart failure (CHF) is one of the leading causes of admission to the hospital [1]. Studies have shown that patients with dilated hearts have a reduction in the frequency of hospital admission and prolongation of life with the implantation of bi-ventricular pacemakers and automatic implantable cardiac defibrillators [AICDs, 2-6]. Recently, "piggybacking" technology onto AICDs and bi-ventricular pacemakers for sensing the progression of impending CHF to reduce the number and length of stay of hospital admissions for CHF has been proposed [7-18]. There are two clinically tested "piggybacked" heart failure warning systems placed on bi-ventricular pacemakers and AICDs to reduce hospital admissions. First, Chronicle® measures right heart pressures in an attempt to monitor increases that are indicative of heart failure [11-13]. Second, Optivol® and CorVue® use lung conductance measurements as an indication of pulmonary edema [8-10, 15]. However, both are downstream measures of the earliest indicator of impending heart failure—left ventricular (LV) preload or left ventricular end-diastolic volume (LVEDV).

Conductance measurements have been available as an invasive tool to detect instantaneous LV volume since 1981 [25, 26]. Conductance tetrapolar electrodes are usually placed on a lead located within the heart chamber to determine instantaneous volume (FIG. 2). Conductance systems generate an electric field (22) using a current source and volume is determined from the returning voltage signal. Prior art shows how to separate the blood and muscle components from the combined voltage signal to determine LV preload from previously implanted AICD and bi-ventricular pacemakers.

Significant improvement in patient care could be achieved by adding the admittance apparatus [19-24] to pacemakers and AICDs, using currently deployed bi-ventricular and AICD leads, to electrically detect either true LV preload, or an increase in LV preload from baseline. Bi-ventricular and the RV AICD leads are already located in the ideal locations—the lateral LV epicardium and the right ventricular (RV) septum (FIGS. 1a, 1b). Since blood has 5-fold lower resistivity than myocardium, the preferential path (22) for a substantial fraction of the current flow will be the LV blood volume. This low-power admittance apparatus can be "piggy-backed" onto implanted AICD and bi-ventricular pacemakers to serve as an early warning system for impending heart failure. Piggy-backed means one can take an existing pacemaker design and add this apparatus to it, without major redesign of the pacemaker itself. This means the admittance circuits need not be included in one of the internal pacemaker chips; rather, it could be added to the system without redesigning the pacemaker circuits themselves. This is particularly true because much of this invention involves a change in software requiring only modest changes in hardware. particular, the apparatus uses the same leads, the same communication channel, and the same power source as the pacemaker. The apparatus can be triggered by the pacemaker or it can run untriggered (i.e., it runs periodically). The output of the apparatus will be a true/false warning signal, or a quantitative measure of heart volume. In this configuration, the apparatus does not alter how the pacemaker operates.

On the other hand, if one wished to design a new pacemaker, this apparatus can also be used to dynamically adjust parameters in the pacemaker itself to maximize heart pumping efficiency. Furthermore, the volume information could be used to improve the effectiveness of ventricular tachycardia detection in an automatic defibrillator.

A version of this apparatus can be implanted in animals (including, but not limited to mice, rats, dogs, and pigs), which includes a pressure channel and a wireless link (FIGS. 5 and 14). The lead is placed in a ventricle (FIG. 2), and the experiment duration can vary from 1 day to 6 months. The duration of the experiment is limited by the animal survival and the storage capacity of the battery, and not the operation of the apparatus. The apparatus measures heart muscle function (left ventricular pressure-volume relationships) in these animals, and can be used for new drug discovery. These animals must be un-tethered and freely roaming so that the transmitted signals are physiologic. The apparatus transmits pressure-volume data (52), and a computer-based receiver collects, displays, and stores the data.

There are two papers describing a technique to detect heart failure [27-28] that may seem similar to the approach herein. In this technique, the current source and sink electrodes are both in the RV, and the sensing electrodes on the LV free wall. This means the electrical field will be confined to the RV. So even though they have sensing electrodes on the LV wall, their signal will have a very weak dependence on the left heart volume, detecting only fringing fields. Their type of measurement is very noise prone, and this problem worsens as the heart enlarges because the septum blocks much of the field from reaching the LV free wall. It is believed that the present invention is superior because 1) the majority of the sensing field goes across the blood pool in the left ventricle due to the relative conductivity of blood being high, and source and sink electrodes being placed on opposite sides of the LV, and 2) because the heart muscle is removed as an artifact of the measurement using admittance. Therefore, it is believed there are no available or proposed technologies that can perform chronic volume measurements of the left ventricle, including LVEDV, LVESV, and LVSV.

BRIEF SUMMARY OF THE INVENTION

The present invention pertains to a method for measuring complex electrical admittance and/or complex electrical impedance in animal or human patients. The method comprises the steps of stimulating with a stimulator disposed in a housing disposed in the patient with two or more electrodes disposed in the patient with either current or voltage. There is the step of sensing with a sensor disposed in the housing with two or more sensing electrodes disposed in the patient to sense a response from the sensing electrodes based on the stimulation of the stimulating electrodes. There is the step of determining with a signal processor disposed in the housing and in electrical communication with both the stimulator and the sensor the complex electrical admittance and/or complex electrical impedance of the patient, the stimulator and the sensor and the signal processor together using less than an average current of less than 23 mA in operation over time at a voltage less than 3.7 V.

The present invention pertains to an apparatus for measuring complex electrical admittance and/or complex electrical impedance in animal or human patients. The apparatus comprises a first electrode and at least a second electrode which are adapted to be disposed in the patient. The apparatus comprises a housing adapted to be disposed in the patient, the housing having disposed in it a stimulator in electrical communication with at least the first electrode to stimulate the first electrode with either current or voltage, a sensor in electrical communication with at least the second electrode to sense a response from the second electrode based on the stimulation of the first electrode, and a signal processor in electrical communication with the sensor to determine the complex electrical admittance or impedance of the patient, the stimulator and the sensor and the signal processor together using less than an average current of less than 23 mA in operation over time.

The present invention pertains to a method for measuring complex electrical admittance and/or complex electrical impedance in animal or human patients. The method comprises the steps of stimulating with a stimulator disposed in a housing disposed in the patient with at least two stimulating electrodes disposed in the patient with either current or voltage. There is the step of sensing with a sensor disposed in the housing with at least two sensing electrodes disposed in the patient to sense a response from the sensing electrodes based on the stimulation of the simulating electrodes. There is the step of determining with a signal processor disposed in the housing and in electrical communication with the sensor the complex electrical admittance or impedance of the patient, the stimulator and the sensor and the signal processor together using less than an average current of less than 23 mA in operation over time.

BRIEF DESCRIPTION OF THE SEVERAL VIEWS OF THE DRAWING

In the accompanying drawings, the preferred embodiment of the invention and preferred methods of practicing the invention are illustrated in which:

FIGS. 10a and 10b show experimental data showing the analog power supply during chirping.

DETAILED DESCRIPTION OF THE INVENTION

Figure 1A:
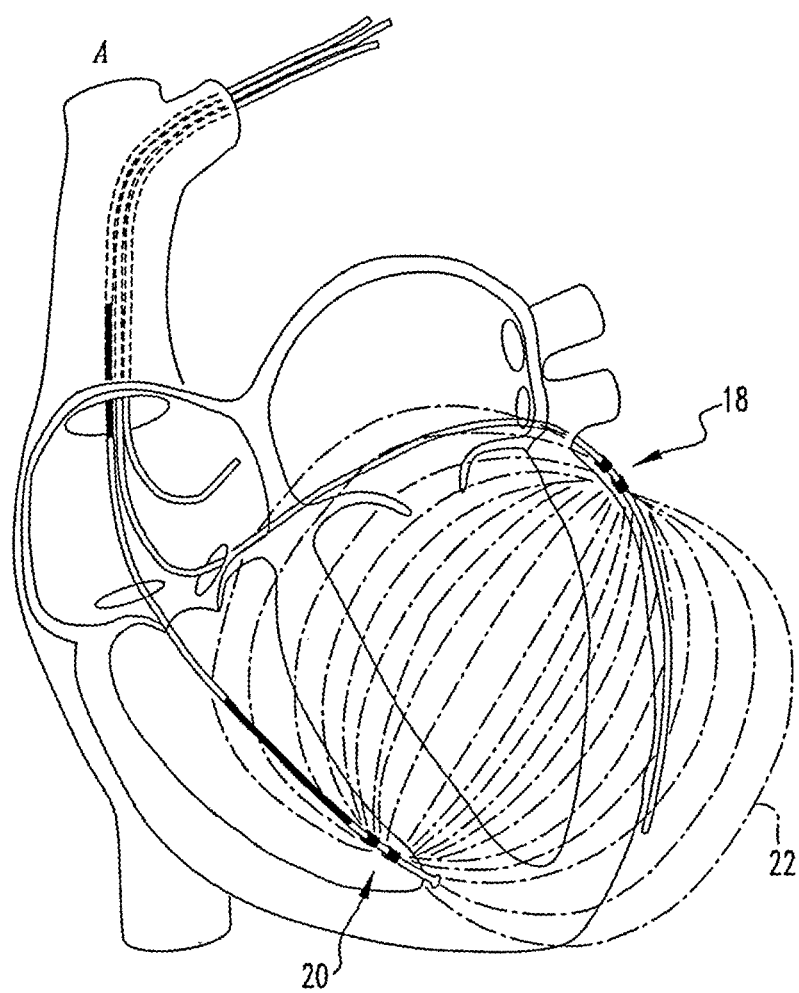
FIGS. 1a and 1b show four electrodes placed in or around the heart using two or more leads.
Figure 1B:
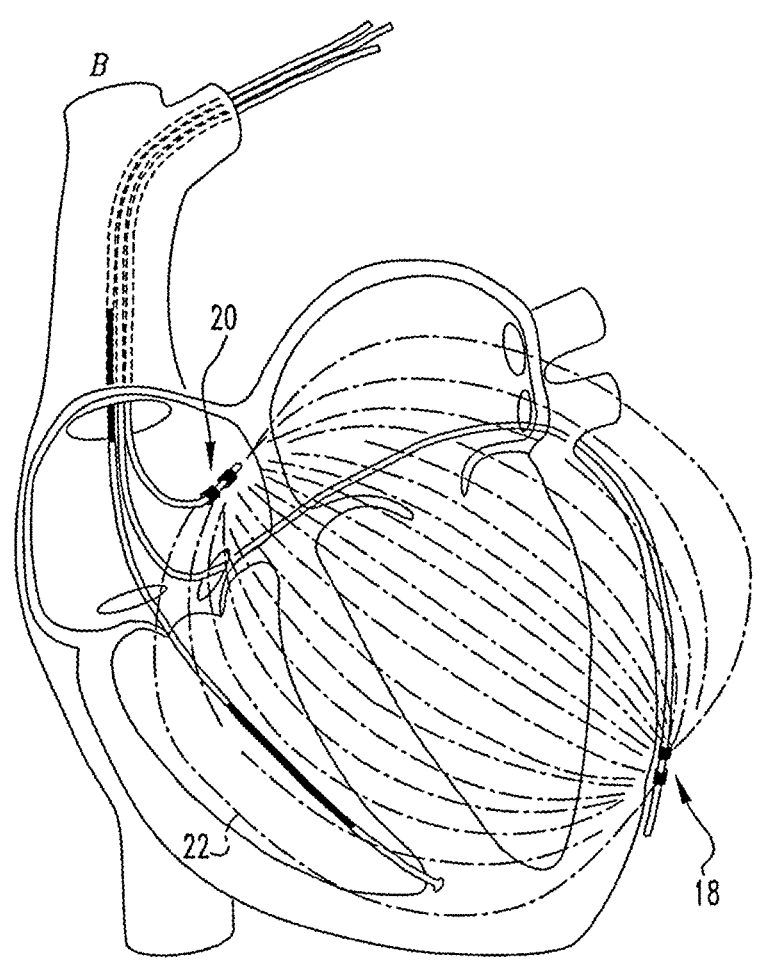
Figure 2:
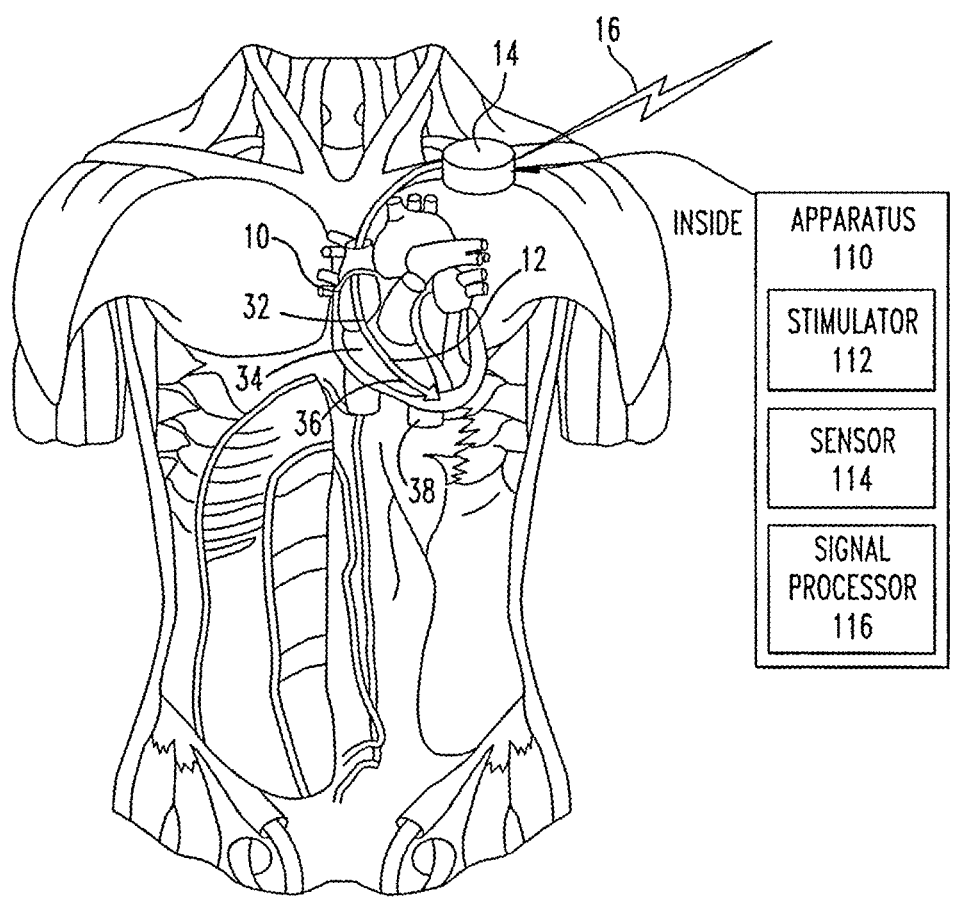
FIG. 2 shows a single four-electrode lead placed in a ventricle.

Referring now to the drawings wherein like reference numerals refer to similar or identical parts throughout the several views, and more specifically to FIGS. 1a, 1b and 2 thereof, there is shown an apparatus 100 for measuring complex electrical admittance and/or complex electrical impedance in animal or human patients. The apparatus 100 comprises two or more electrodes 10 that are adapted to be disposed in the patient. The apparatus 100 comprises a housing 110 adapted to be disposed in the patient. The housing 110 has disposed in it a stimulator 112 in electrical communication with two or more electrodes 10 to stimulate with either current or voltage, a sensor 114 in electrical communication with the same stimulating electrodes 10 or with additional electrodes 10 to sense a response based on the stimulation of the stimulating electrodes 10, and a signal processor 116 in electrical communication with both the stimulator 112 and the sensor 114 to determine the complex electrical admittance or impedance of the patient. The stimulator 112 and the sensor 114 and the signal processor 116 together use less than an average current of less than 23 mA in operation over time.

The present invention pertains to a method for measuring complex electrical admittance and/or complex electrical impedance in animal or human patients. The method comprises the steps of stimulating with a stimulator 112 disposed in a housing 110 disposed in the patient with two or more electrodes 10 disposed in the patient with either current or voltage. There is the step of sensing with a sensor 114 disposed in the housing 110 with two or more sensing electrodes 10 disposed in the patient to sense a response from the sensing electrodes 10 based on the stimulation of the stimulating electrodes 10. There is the step of determining with a signal processor 116 disposed in the housing 110 and in electrical communication with both the stimulator 112 and the sensor 114 the complex electrical admittance and/or complex electrical impedance of the patient, the stimulator 112 and the sensor 114 and the signal processor 116 together using less than an average current of less than 23 mA in operation over time at a voltage less than 3.7 V.

The present invention pertains to an apparatus 100 for measuring complex electrical admittance and/or complex electrical impedance in animal or human patients. The apparatus 100 comprises a first electrode and at least a second electrode which are adapted to be disposed in the patient. The apparatus 100 comprises a housing 110 adapted to be disposed in the patient, the housing 110 having disposed in it a stimulator 112 in electrical communication with at least the first electrode to stimulate the first electrode with either current or voltage, a sensor 114 in electrical communication with at least the second electrode to sense a response from the second electrode based on the stimulation of the first electrode, and a signal processor 116 in electrical communication with the sensor 114 to determine the complex electrical admittance or impedance of the patient, the stimulator 112 and the sensor 114 and the signal processor 116 together using less than an average current of less than 23 mA in operation over time.

The present invention pertains to a method for measuring complex electrical admittance and/or complex electrical impedance in animal or human patients. The method comprises the steps of stimulating with a stimulator 112 disposed in a housing 110 disposed in the patient with at least two stimulating electrodes 10 disposed in the patient with either current or voltage. There is the step of sensing with a sensor 114 disposed in the housing 110 with at least two sensing electrodes 10 disposed in the patient to sense a response from the sensing electrodes 10 based on the stimulation of the simulating electrodes 10. There is the step of determining with a signal processor 116 disposed in the housing 110 and in electrical communication with the sensor 114 the complex electrical admittance or impedance of the patient, the stimulator 112 and the sensor 114 and the signal processor 116 together using less than an average current of less than 23 mA in operation over time.

The present invention pertains to an apparatus 100 for measuring complex electrical admittance and/or complex electrical impedance in animal or human patients. The apparatus 100 comprises two or more electrodes 10 that are adapted to be disposed in the patient. The apparatus 100 comprises a housing 110 adapted to be disposed in the patient. The housing 110 has disposed in it a stimulator 112 in electrical communication with two or more electrodes 10 to stimulate with either current or voltage, a sensor 114 in electrical communication with the same stimulating electrodes 10 or with additional electrodes 10 to sense a response based on the stimulation of the stimulating electrodes 10, and a signal processor 116 in electrical communication with both the stimulator 112 and the sensor 114 to determine the complex electrical admittance or impedance of the patient. The stimulator 112 and the sensor 114 and the signal processor 116 together use less than an average current of less than 23 mA in operation over time.

The signal processor 116 may measure a real part, an imaginary part, a magnitude, and/or phase of admittance. The signal processor 116 may measure a real part, an imaginary part, a magnitude, and/or phase of impedance can be measured. The stimulator 112 may produce an excitation wave that is a sinusoid at a single frequency, greater than 0 and less than or equal to 1 MHz. The stimulator 112 may produce an excitation wave that is two or more sinusoids with frequencies greater than 0 and less than or equal to 1 MHz. The stimulator 112 may produce an excitation wave that is any shape that can be defined by a repeated sequence of integer values, whose frequency components range from 0 to 1 MHz.

The stimulator 112 may produce an excitation wave that is created by a resistor-summing network, called a SinDAC, such that a number of resistors, resistor values, digital output sequence, and rate of digital outputs are selected to define a shape and frequency of the excitation wave. An ADC conversion of the sensor 114 may be synchronized to the SinDAC outputs generating the stimulation. A Discrete Fourier Transform (DFT) may be used by the signal processor 116 to extract complex electrical properties.

The complex measurements may occur with an analog circuit using a synchronous demodulator to directly measure either impedance or admittance. While measuring complex electrical properties 100 times a second may require less than 500 µA of current. While measuring complex electrical properties 50 times an hour may require less than 1 µA of current.

The size of the housing 110 may be less than 2 cm by 2 cm by 0.4 cm. The electrodes 10 may be placed in or on the heart, which are used to estimate heart volume, stroke volume, change in heart volume, and/or change in stroke volume of the patient. The apparatus 100 may include a pressure sensor 114 disposed on the lead, which is used to measure pressure volume loops in the heart. The apparatus 100 may include a wireless link and recording base station 118 which are used to remotely measure pressure, heart volume, stroke volume, change in heart volume, and/or change in stroke volume of the patient. The housing 110 may include a pacemaker.

In the operation of the invention, a low-power method and apparatus 100 has been designed to measure electrical impedance and electrical admittance in, on, and across the heart. Electrical impedance (Z) is the ratio of the effort divided by flow as electrical energy flows through an object. Electrical admittance (Y) is the ratio of flow divided by effort. The impedance and admittance of living tissue are complex numbers; this means electrical energy is both reduced in amplitude and delayed in time (phase shift) by the tissue during transfer. The electrical measurements can be used to determine heart volume, change in heart volume, and/or stroke volume. Prior art has defined the lead and the relationship between electrical properties and heart physiology. Herein is presented in substantial detail several possible embodiments of a method and apparatus 100, used to measure the electrical properties, that is both low in power and small in size. Other technically-similar embodiments using the same overall power-saving strategies will likely prove equally effective in making these measurements.

The apparatus 100 can be used in telemetric applications of heart muscle function in animals. There is a desire to develop a low power, small sized, implantable systems to last up to six months. Using the low-power strategy that is described herein will make it possible to implant the apparatus 100 in animals to study the long term effect of drug therapies for treating cardiac diseases. For instance, it can be used in gene-altered mouse hearts for new drug discovery. Animals with these implantable apparatuses would be untethered, and freely roaming.

More importantly, the apparatus 100 can be incorporated into existing pacemakers and used to detect early-stage congestive heart failure. Given the apparatus 100, the doctors will be able to adjust drug doses and prevent costly hospital visits.

The apparatus 100 could also be used in an adaptive pacemaker to adjust the timing of the electrical stimulations in order to maximize heart pumping efficiency.

In summary, a technique and an apparatus 100 has been developed, which is both low power and small size, capable of measuring heart volume, change in heart volume, stroke volume, and/or change in stroke volume.

10—Four Electrodes for Admittance Measurement, Located in the Ventricle

One example of an existing four-electrode lead is the Scisense FTE1-1912B-8018. This is a 1.9 F Pressure-Volume Lead. This is a flexible and soft rat pressure-volume lead with an 8 mm ring spacing for use with average sized rats. The diameter is 1.9 F and the distance from electrodes 1, 2 to electrodes 3, 4 is about 10 mm. In addition, the electrodes on existing leads of existing products (see description of pacemaker 14) can be used with humans.

12—a Single Lead Placed in the Ventricle

FIGS. 1a and 1b show the lead (10) in the right ventricle.

14—the Present Invention can be Added to or Embedded into Existing Products

Two examples of existing products (pacemakers) into which the apparatus 100 could be embedded is Optivol® (Medtronic, Minneapolis, Minn.) and CorVue® (St. Jude Medical, St. Paul, Minn.). When embedding the apparatus 100 into an existing apparatus, the existing apparatus will include a housing 110 and power supply. The Medtronic InSync® ICD model 7272 housing 110 is box-shaped with 8 mm radius curves on all edges. The outside dimensions of its metal case are 57 mm wide, 72 mm tall, 16 mm tall. The metal shell is 1 mm thick and is made from a titanium alloy. There is a plastic connector on top with dimensions 35 mm wide, 20 mm tall, 15 mm wide. Over 50% of the internal space is occupied by the lithium battery. Many pacemakers use lithium/iodine-polyvinylpyridine primary batteries, which can last 8 to 10 years. The housing 110 of the apparatus 100 can be smaller since the components of the invention can be smaller. The size without battery and lead can be smaller than 11 mL, such as 9 mL or 7 mL or 5 mL. The weight can be less than 9 g, such as 7 g or 5 g or 4 g. The average power=current*3.6V to operate the sensor 114, stimulator 112 and signal processor 116 can be less than 86 mW, such as 75 mW or 65 mW or 55 mW or 35 mW. The average current to operate the sensor 114, stimulator 112 and signal processor 116 can be less than 24 mA, such as 20 mA or 17 mA or 14 mA. The current while sampling with the sensor 114, stimulator 112 and signal processor 116 can be less than 42 mA, such as 35 mA or 28 mA or 22 mA. See table 1 below which identifies these various properties in terms of what has been actually built and is operative for the technique described herein.

16—the System can Communicate with the Patient or Medical Staff

Existing wireless protocols such as SimpliciTI™ by Texas Instruments are used for wireless communication.

18—Electrodes 1 and 2 Placed on the Heart (in a Coronary Vein)

One example of an existing lead that can be positioned in the coronary vein is the St. Jude Quicksite XL 1058T. It is 75.86 cm long. It has a diameter of 5.0 F at the distal lead and a diameter of the 5.6 F at the proximal lead. The lead (18) is positioned into the coronary vein during implantation surgery. The veins are on the epicardial surface of the heart. The position of electrodes 1, 2 of the lead will be fixed relative to the position of the vein by the scarring occurring at the insertion site of the lead where it enters the vein. In other words, electrodes 1, 2 will be at a fixed position on the epicardial surface of the heart. Because the heart is beating, electrodes 1, 2 will move relative to electrodes 3, 4.

20—Electrodes 3 and 4 Placed in the Heart (in a Ventricle or Atrium)

One example of an existing lead that can be positioned in the right ventricle is the St Jude Tendril SDX 1688TC. This lead is bipolar, can be used in the atria or ventricle. It has a screw-in electrode. It comes in lengths of 34, 40, 46, 52, 58, 85, 100 cm. It uses a 7F introducer. One example of an existing lead that can be positioned in the right atrium is the St Jude Optisense 1699TC. This is a pacing bipolar electrode and is also 7F in diameter. It comes in lengths of 40 46 and 52 cm.

The lead (20) is positioned into either the apex of the right ventricle or into the right atrium. This lead is inserted via the systemic veins and subsequently screwed into the myocardial tissue. Therefore, electrodes 3 and 4 are fixed on the endocardial surface of either the right ventricle or right atrium. The distance between electrode pair 1, 2 and pair 3, 4 will be about 70 to 100 cm, and will vary as the heart beats. When using lead (10), the distance between 1, 2 and 3, 4 is fixed. When using lead (18) and (20), the distance between 1, 2 and 3, 4 is variable. This variable distance is incorporated into the equation used to convert blood resistance to volume (92).

When using lead 10, the distance between 1, 2 and 3, 4 is fixed. When using lead 18 and 20, the distance between 1, 2 and 3, 4 is variable. This variable distance is incorporated into the equation used to convert blood resistance to volume (92).

24—Microcontroller or Digital Logic

One example of an existing microcontroller that can be used with the apparatus 100 is the Texas Instruments MSP430F2013. This microcontroller has 2048 bytes of Flash EEPROM, 128 bytes of RAM, and runs at 16 MHz. It can be used to measure volume, and comes in a 16-pin surface mount package occupying about 4 by 4 by 1 mm.

41—Pressure Sensor (Optional)

One example of an existing pressure sensor is the one included on the Scisense FTE1-1912B-8018 lead. This is a 1.9 F Pressure-Volume Lead.

42—Low Power Amplifier and 43—Low Power Amplifier for the Pressure Channel

One example of a low power amplifier is the Texas Instruments INA322. This instrumentation amp runs with 490 μA of supply current, and has bandwidth of 2 MHz at a gain of 25.

56—Antenna Used to Send Wireless Communication

One example of an antenna is the ANT-916-CHP antenna from Antenna Factor. It is a surface mount part that operates at 916 MHz.

84—Discrete Fourier Transform

The Discrete Fourier Transform converts signals in the time domain into the frequency domain.

The four-electrode leads and there placement, shown in FIG. 1a, FIG. 1b and FIG. 2 are well known to one skilled in the art. The four electrodes (32, 34, 36, 38, shown in FIGS. 4 and 5) are either placed around the heart as shown in FIG. 1a and FIG. 1b, or in the heart as shown in FIG. 2. A sinusoidal current is applied to electrodes 1 (32) and 4 (38), and the resulting voltage is measured between electrodes 2 (34) and 3 (36). Although the description refers to a four-electrode configuration, the technique here will also operate with any configuration using 2 or more electrodes. If the number of electrodes is less than four, then either or both electrode pairs 1-2 or 3-4 are shared. When using more than 4 electrodes, two electrodes are used to supply the sinusoidal current, and the remaining electrodes are used in pairs to measure the volume between the electrode pairs. The methods that convert electrical measurements into heart volumes are also well known to one skilled in the art. The method to remove the muscle component from the conductance and admittance signals is well known to one skilled in the art. (See patents and applications in reference list below). This present invention focuses on conversion to practice that is both small in size and extremely low in power.

The fundamental theory uses the Discrete Fourier Transform (DFT). The input to the DFT will be N samples versus time, and the output will be N points in the frequency domain. The sampling rate is defined as L.

$$\text{Input}:\{x_n\}=\{x_0,x_1,x_2,\ldots,x_{N-1}\}$$

$$\text{Output}:\{X_k\}=\{X_0,X_1,X_2,\ldots,X_{N-1}\}$$

The definition of the DFT is $$X_k = \sum_{n=0}^{N-1} x_n W_N^{kn} \text{ where}$$

$$W_N = e^{-j2\pi/N} \quad k = 0, 1, 2, \ldots, N-1$$

The DFT output $X_k$ at index k represents the amplitude and phase of the input at frequency $k*f_s/N$ (in Hz). The SinDAC output and the ADC input occur at $f_s$. An ADC sample occurs every time $T=1/f_s$. If M is the number of SinDAC outputs per wave, then the sinusoidal frequency f is $f_s/M$. The DFT resolution in Hz/bin is the reciprocal of the total time spent gathering time samples; i.e., $1/(N*T)=f_s/N$. To measure the voltage response at frequency f, set $f_s/M=k*f_s/N$, and look at just the one term, k=N/M. Recall that both $M=2^m$ and $N=2^n$ are powers of 2, where m and n are integers with n greater than or equal to m. This means k will also be a power of 2, which will greatly simplify the calculation of the DFT for the one point at k. The number of periods in the sample space will be N/M. Since the excitation is constant current, the calculated voltage response is a measure of impedance. Although, it will be lower power to set N/M to be a power of 2, the method will work for any integers {N, M} such that N/M is an integer.

Figure 4:
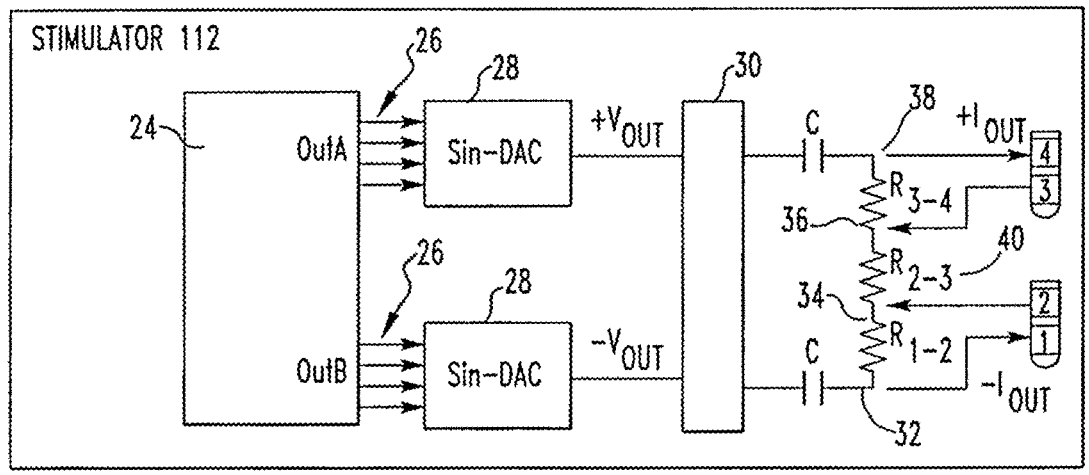
FIG. 4 is a block diagram of the current stimulation portion of the apparatus.
Figure 5:
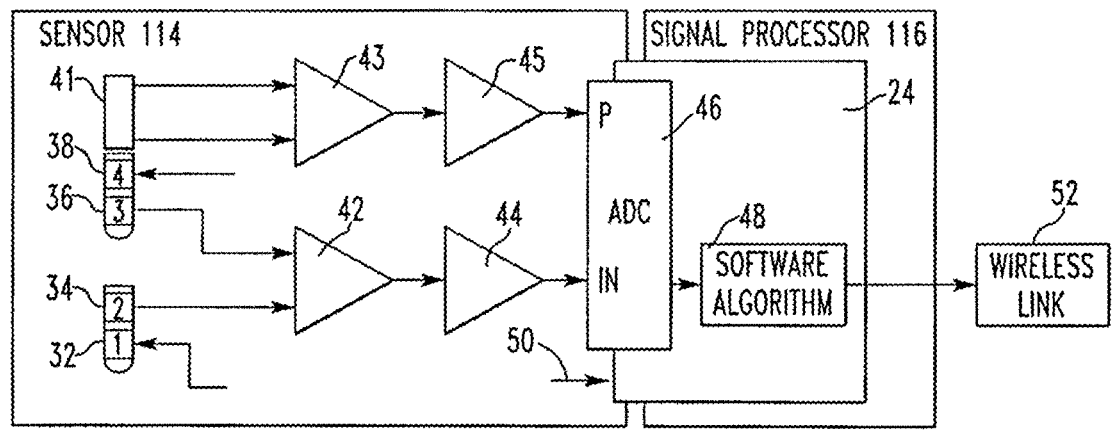
FIG. 5 is a block diagram of the voltage sensing portion of the apparatus, with optional pressure, and with optional wireless link.

Three specific illustrative examples are given, but the method will work for any integers {N, M} such that N/M is an integer. In the first example, let f=5 kHz, M=8, and N=16. FIG. 4 shows a block diagram of the constant current output circuit. The microcontroller (24) writes digital values (26) to the SinDAC (28) at a rate of $f_s=M*f=40$ kHz. With $f_s$ equal to 40 kHz, the time between samples is $\Delta t=25$ μs. The circuit (30) drives lead pins 1 (32) and 4 (38) with an AC current of constant amplitude and a frequency of 5 kHz. FIG. 5 shows a block diagram of the voltage sensing input circuit.

The differential voltage across lead pins 2 (34) and 3 (36) is amplified (42) and filtered (44). The filter (44) is optional, meaning the apparatus 100 will function without it, reducing power at the expense of reduced signal/noise ratio. The resulting signal is sampled by the ADC (46) at the same $f_s=40$ kHz rate. A total of N=16 data points (two periods) are collected with a total sample time=400 μs. The input sampling rate is synchronized to the output rate of the two SinDACs. Let the sampled inputs be $x_0, x_1, x_2, \ldots, x_{15}$. Since the sampling rate is 40 kHz, the k=2 term represents 5 kHz. In other words, $X_2$ represents complex impedance at f=5 kHz. For an N=16 DFT, calculate the complex constants:

$$W^k=\exp(-2\pi ik/16)=\cos(2\pi k/16)-i*\sin(2\pi k/16)$$

If M and N are powers of two, the DFT term at k=N/M will be very simple to calculate—this is the essence of the well-known Fast Fourier Transform (FFT) algorithm, which is presently in wide-spread use. In this first example, to calculate the k=2 term, only every other $W^k$ term is needed:

$$\text{Re } Z=\text{Re}[Z_2]=x_0-x_4+x_8-x_{12}+\sqrt{\tfrac{1}{2}}*(x_1-x_3-x_5+x_7+x_9-x_{11}-x_{13}+x_{15})$$

$$\text{Im } Z=\text{Im}[Z_2]=-x_2+x_6-x_{10}+x_{14}+\sqrt{\tfrac{1}{2}}*(-x_1-x_3+x_5+x_7-x_9-x_{11}+x_{13}+x_{15})$$

Prior implementations measured magnitude and phase, and then calculated the real and imaginary parts using trigonometric functions. It is not needed to calculate magnitude and phase. However, if desired magnitude and phase could be calculated as $$\text{Mag}|Z_2|=\text{sqrt}(\text{Re}[Z_2]*\text{Re}[Z_2]+\text{Im}[Z_2]*\text{Im}[Z_2])$$

$$\text{Angle}(Z_2)=\arctan(\text{Im}[Z_2]/\text{Re}[Z_2])$$

$\sqrt{\tfrac{1}{2}}$ can be approximated as a fixed-point number with sufficient accuracy. Because the input to the lead system is constant current, the output is the real and imaginary part of the impedance at 5 kHz. Let Z be the complex impedance for the k=2 term $$Z=\text{Re } Z+j \text{ Im } Z$$

One possible fixed-point implementation (48) is $$\text{Re } Z=(17*(x_0-x_4+x_8-x_{12})+12*(x_1-x_3-x_5+x_7+x_9-x_{11}-x_{13}+x_{15}))/16$$

$$\text{Im } Z=(17*(-x_2+x_6-x_{10}+x_{14})+12*(-x_1-x_3+x_5+x_7-x_9-x_{11}+x_{13}+x_{15}))/16$$

The "16" in the above equations is arbitrary because the apparatus 100 will be calibrated. As an example of a low-power multiply, consider the simple case of 17*x. The "multiply by 17" is rewritten as a "multiply by 16" plus the addition of the input. In this way, the algorithm can be implemented on a low-power microcontroller, as shown in the following pseudo-code. These three steps require one store, 4 shifts and 1 addition.

1) Set CopyOfX equal to x
2) Shift x left 4 times
3) Add CopyOfX to x

As a second example, let f=20 kHz, M=8, and N=32. The microcontroller (24) writes digital values (26) to the SinDAC (28) at a rate of $f_s=M*f=160$ kHz. With $f_s$ equal to 160 kHz, the time between samples is $\Delta t=6.25$ μs. The circuit (30) drives lead pins 1 (32) and 4 (38) with a 20 kHz AC current. The voltage signal is sampled by the ADC (46) at the same $f_s=160$ kHz rate. In this particular example a total of N=32 data points are collected with a total sample time=200 μs—in fact, any convenient multiple of 2 can be used, so N=32 is just for illustration. Let the sampled inputs be $x_0, x_1, x_2, \ldots, x_{31}$. Since the sampling rate is 160 kHz, the k=4 term represents the desired 20 kHz. In other words, $X_4$ represents complex impedance at f=20 kHz. For a 32-point DFT, calculate the complex constants:

$$W^k = \exp(-2\pi i k/32) = \cos(2\pi k/32) - i \sin(2\pi k/32)$$

The k=4 represents f=20 kHz. To calculate the k=4 term, only every fourth $W^k$ term is needed:

$$\text{Re } Z = \text{Re}[Z_4] = x_0 - x_4 + x_8 - x_{12} + x_{16} - x_{20} + x_{24} - x_{28} + \sqrt{1/2} \ast (x_1 - x_3 - x_5 + x_7 + x_9 - x_{11} - x_{13} + x_{15} + x_{17} - x_{19} - x_{21} + x_{23} + x_{25} - x_{27} - x_{29} + x_{31})$$

$$\text{Im } Z = \text{Im}[Z_4] = -x_2 + x_6 - x_{10} + x_{14} - x_{18} + x_{22} - x_{26} + x_{30} + \sqrt{1/2} \ast (-x_1 - x_3 + x_5 + x_7 - x_9 - x_{11} + x_{13} + x_{15} - x_{17} - x_{19} + x_{23} - x_{25} - x_{27} + x_{29} + x_{31})$$

Again, it is not need here to calculate magnitude and phase. Other systems measure magnitude, |Z|, with or without phase angle, $\varphi$. These older systems then use trigonometry to determine the real and imaginary part of the signal. The following equations are presented only as a comparison to prior art.

$$\text{Re } Z = |Z| \ast \cos(\varphi)$$

$$\text{Im } Z = |Z| \ast \sin(\varphi)$$

Again, $W^k$ terms can be approximated as a fixed-point numbers. Notice how close 12/17 is to the $\sqrt{1/2}$ (0.70588 versus 0.70711). Using fixed-point saves power. Let Z be the complex impedance for the k=4 term. One possible fixed-point implementation (48) is $$\text{Re } Z = (17 \ast (x_0 - x_4 + x_8 - x_{12} + x_{16} - x_{20} + x_{24} - x_{28}) + 12 \ast (x_1 - x_3 - x_5 + x_7 + x_9 - x_{11} - x_{13} + x_{15} + x_{17} - x_{19} - x_{21} + x_{23} + x_{25} - x_{27} - x_{29} + x_{31}))/32$$

$$\text{Im } Z = (17 \ast (-x_2 + x_6 - x_{10} + x_{14} - x_{18} + x_{22} - x_{26} + x_{30}) + 12 \ast (-x_1 - x_3 + x_5 + x_7 - x_9 - x_{11} + x_{13} + x_{15} - x_{17} - x_{19} + x_{23} - x_{25} - x_{27} + x_{29} + x_{31}))/32$$

The divide by 32, implemented as a right shift, was added to adjust the amplitude of the calculation. Because the apparatus 100 will be calibrated, the "32" in these equations is arbitrary.

As a third example, let f=10 kHz, M=12, and N=24. The microcontroller (24) writes digital values (26) to the SinDAC (28) at a rate of $f_s = M \ast f = 120$ kHz. With $f_s$ equal to 120 kHz, the time between samples is $\Delta t = 8.33$ μs. The circuit (30) drives lead pins 1 (32) and 4 (38) with a 10 kHz AC current. The voltage signal is sampled by the ADC (46) at the same $f_s = 120$ kHz rate. In this particular example total of N=24 data points are collected with a total sample time=200 μs—in fact, any k=N/M equal to an integer will work, so N=24 is just for illustration. Let the sampled inputs be $x_0, x_1, x_2, \ldots, x_{23}$. Since the sampling rate is 120 kHz, the k=2 term represents the desired 10 kHz. In other words, $X_2$ represents complex impedance at f=10 kHz. For a 24-point DFT, calculate the complex constants:

$$W^k = \exp(-2\pi i k/24) = \cos(2\pi k/24) - i \sin(2\pi k/24)$$

The k=2 represents f=10 kHz. Notice that $\cos(\pi/6) = \sqrt{3}/4 = 0.8660$. To calculate the k=2 term, only need every second $W^k$ term is needed:

$$\text{Re}[Z_2] = x_0 - x_6 + x_{12} - x_{18} + \sqrt{3}/4 \ast (x_1 - x_5 - x_7 + x_{11} + x_{13} - x_{17} - x_{19} + x_{23}) + 1/2 \ast (x_2 - x_4 - x_8 + x_{10} + x_{14} - x_{16} - x_{20} + x_{22})$$

$$\text{Im}[Z_2] = -x_3 + x_9 - x_{15} + x_{21} + 1/2 \ast (-x_1 - x_5 + x_7 + x_{11} - x_{13} - x_{17} + x_{19} + x_{23}) + \sqrt{3}/4 \ast (-x_2 - x_4 + x_8 + x_{10} - x_{14} - x_{16} + x_{20} + x_{22})$$

These equations can also be implemented in fixed-point math. Notice how close 13/15 is to the $\sqrt{3}/4$ (0.8667 versus 0.8660). Using fixed-point saves power. Let Z be the complex impedance for the k=2 term. The "32" in the following equations is arbitrary because the apparatus 100 will be calibrated:

$$\text{Re}[Z_2]((30 \ast (x_0 - x_6 + x_{12} - x_{18}) + 26 \ast (x_1 - x_5 - x_7 + x_{11} + x_{13} - x_{17} - x_{19} + x_{23}) + 15 \ast (x_2 - x_4 - x_8 + x_{10} + x_{14} - x_{16} - x_{20} + x_{22}))/32$$

$$\text{Im}[Z_2] = ((30 \ast (-x_3 + x_9 - x_{15} + x_{21}) + 15 \ast (-x_1 - x_5 + x_7 + x_{11} - x_{13} - x_{17} + x_{19} + x_{23}) + 26 \ast (-x_2 - x_4 + x_8 + x_{10} - x_{14} - x_{16} + x_{20} + x_{22}))/32$$

An important consequence of the M-to-1 ratio in both the SinDAC and the DFT is that the sampling frequency ($f_s$) need not be accurate. If the input/output sampling rate is either a little too fast or too slow, the system still works. For example, if the sampling frequency drops by 5%, going from 160 kHz to 152 kHz, the only consequence is now the electrical impedance and admittance measurements are being made at 19 kHz instead of 20 kHz. The electrical properties of blood and tissue do not significantly vary for frequencies 19 to 21 kHz, so a 5% error in the clock frequency will not affect the ability of the apparatus 100 to measure heart volume. It requires a significant amount of electrical power to create a precise sampling clock. Conversely, this apparatus 100 can derive its timing from a low-power voltage-controlled oscillator (VCO).

Figure 6:
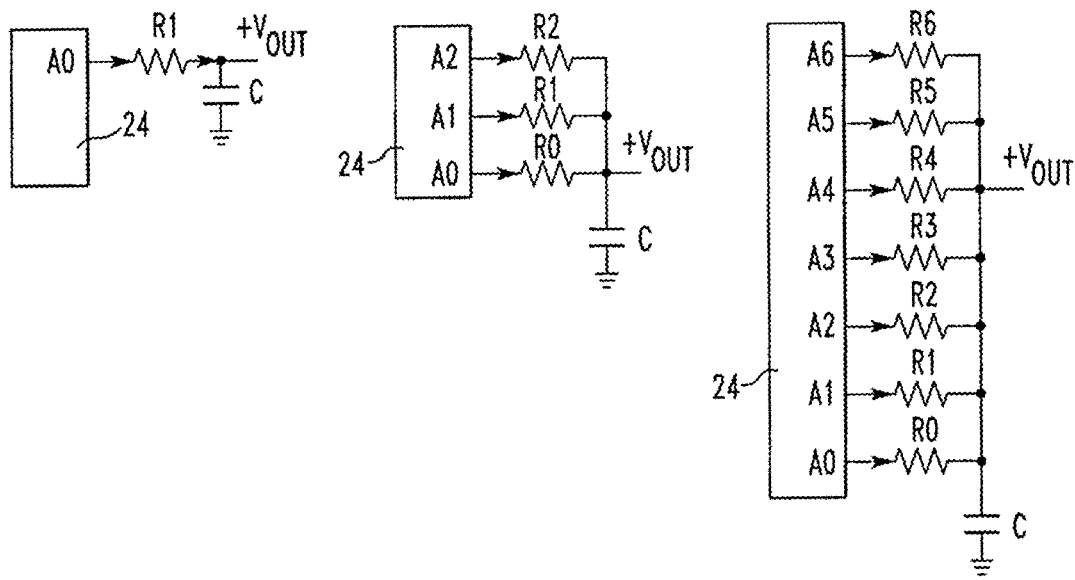
FIG. 6 shows SinDAC used to create sine waves.
Figure 7:
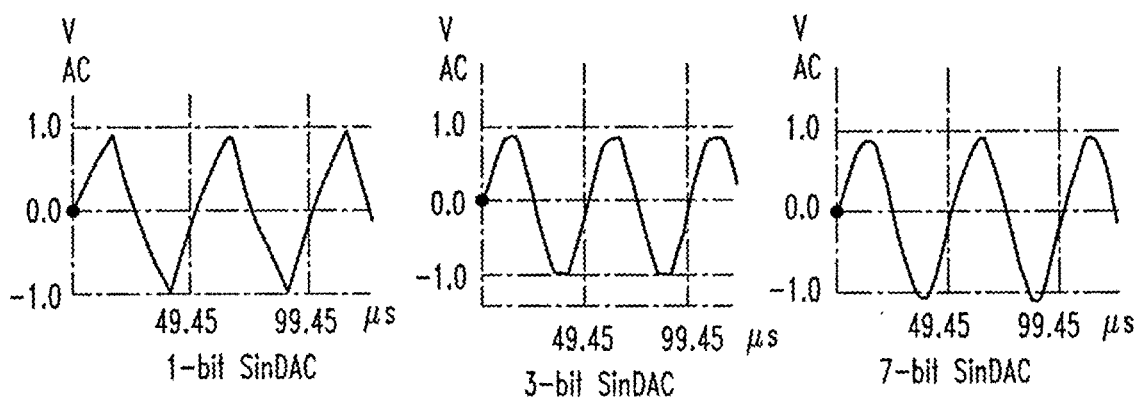
FIG. 7 shows measured outputs from 1-bit, 3-bit, and 7-bit SinDAC implementations.

The basic idea of the SinDAC (28) is shown in FIG. 6. There are one or more digital outputs from the microcontroller (26). Each output will be 0 or +V volts, where +V is the $V_{OH}$ of the CMOS electronics. Each digital output is connected a resistor. The resistor-summing network creates the voltage output of the SinDAC ($V_{out}$). The resistance values and digital output patterns are selected to match the $V_{out}$ output to the desired sine wave. A capacitor can be added to smooth out the voltage output, but good results can be obtained without the capacitor shown in FIG. 6. FIG. 7 shows data measured with three SinDAC implementations, all of which create 20-kHz sinusoids. Let f be the desired sine wave frequency. The 1-bit output pattern is {0, 1} occurring at a rate of 2*f kHz. One possible 8-element output pattern for the 3-bit SinDAC is {0, 1, 3, 7, 7, 6, 4, 0}. Since there are 8 elements in this pattern, the SinDAC output rate should be 8*f. One possible 12-element output pattern for the 5-bit SinDAC is {0, 1, 3, 7, 15, 31, 31, 30, 28, 24, 16, 0}, occurring at a rate of 12*f. One possible 16-element output pattern for the 7-bit SinDAC is {0, 1, 3, 7, 15, 31, 63, 127, 127, 126, 124, 120, 112, 96, 64, 0} occurring at a rate of 16*f. These patterns are specific examples of a general approach with the following five general characteristics:

1) The binary patterns have symmetry, because the sine wave is symmetric. The example patterns listed above were derived from a Johnson Counter, which is an example of a ring counter [29]. In particular, the following n-bit patterns were created using the top n bits of an (n+1)-bit Johnson counter. These patterns include, but are not limited to the following:

1-bit 0, 1

3-bit 000, 001, 011, 111, 111, 110, 100, 000

5-bit 00000, 00001, 00011, 00111, 01111, 11111, 11111, 11110, 11100, 11000, 10000, 00000

7-bit 0000000, 0000001, 0000011, 0000111, 0001111, 0011111, 0111111, 1111111, 1111111, 1111110, 1111100, 1111000, 1110000, 1100000, 1000000, 0000000

The pattern need not be derived from a Johnson counter. For example, these patterns all create 8-element sequences. Any of these patterns could be used to create a sine wave that is 8 times slower than the output rate. I.e., M=8, or $f_s=8*f$.

3-bit 000, 001, 011, 111, 111, 011, 001, 000
3-bit 000, 001, 011, 110, 111, 011, 011, 001
4-bit 0000, 0001, 0011, 0111, 1111, 0111, 0011, 0001
5-bit 00000, 00001, 00111, 01111, 11111, 01111, 00011, 00001
6-bit 000000, 000001, 000111, 011111, 111111, 001111, 000011, 000001

2) The length of the pattern is much shorter than a pattern used by a regular DAC when creating a sine wave.

3) The number of bits is much smaller than an equivalent system using a linear DAC to create a sine wave.

4) The output rate is synchronized with the input rate.

5) A resistor summing circuit converts the binary pattern to a voltage. The individual resistor values determine the weight of each bit. The weighting of each bit is neither equal nor a power of 2. Rather, the resistor values in FIG. 6 are found by minimizing the mean squared error between the desired wave and actual wave using multidimensional minimization techniques. An analog circuit (30) will convert the voltage output to a current.

Figure 3:
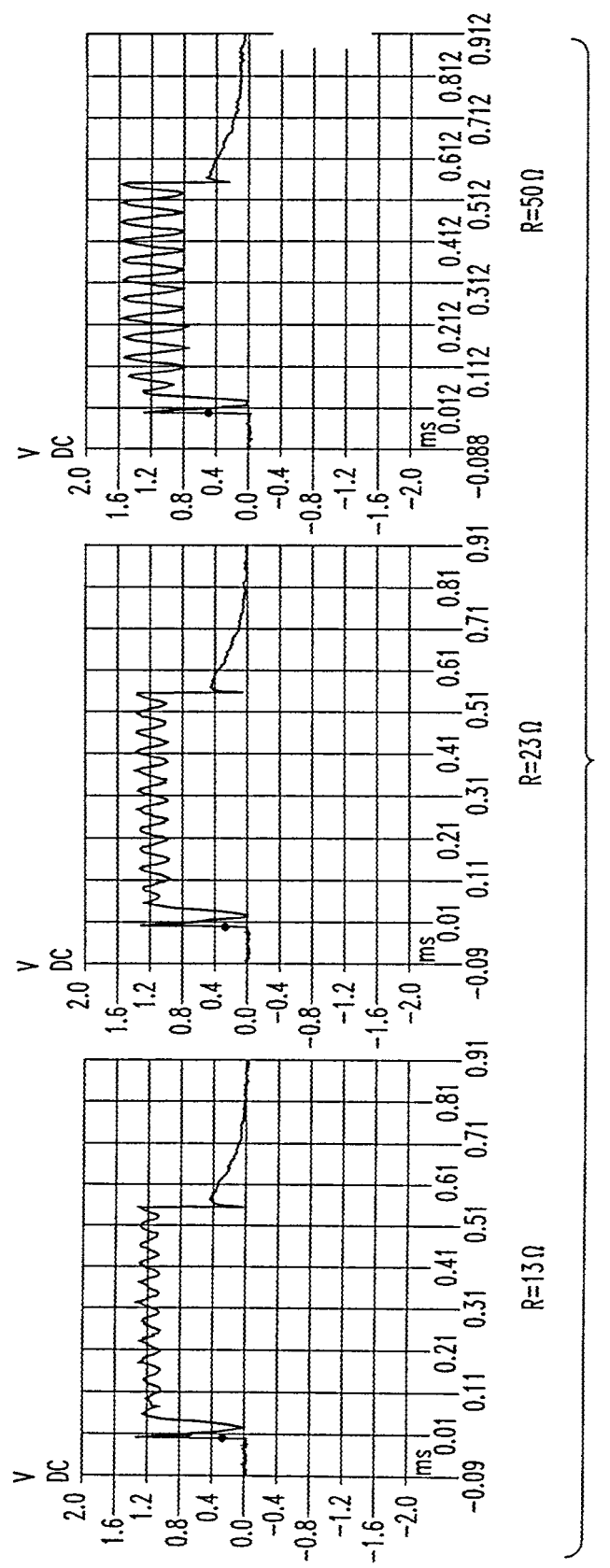
FIG. 3 shows ADC input voltage showing the chirped sinusoid generated by the SinDAC.

The software can be adjusted to select the length of the chirp. FIG. 3 shows the voltage measured from a 20 kHz 12-period chirp lasting 500 μs, generated by a 3-bit SinDAC. The chirped measurement will occur either periodically or using a trigger input. For example, the apparatus 100 could output 50 chirps at 10 Hz once an hour. Taking 50 chirps allows the apparatus 100 to find EDV throughout the cardiac and respiratory cycles. Performing measurements once an hour filters out the position dependence. If there is an ECG trigger at end diastole, then the 50 chirps at 10 Hz can be reduced to 5 chirps every heartbeat.

Figure 8A:
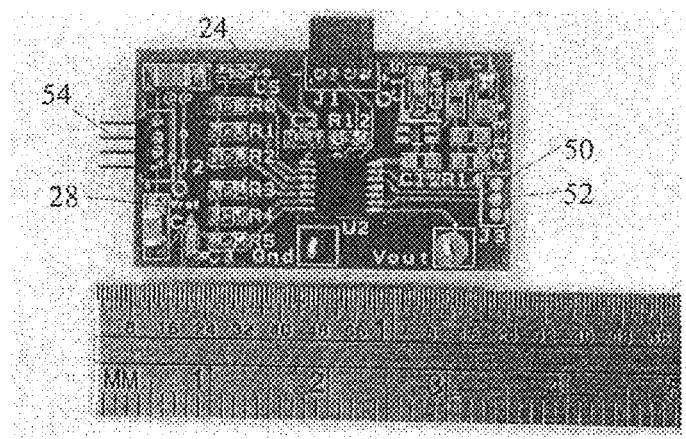
FIGS. 8a and 8b show front and back photographs of a prototype circuit.
Figure 8B:
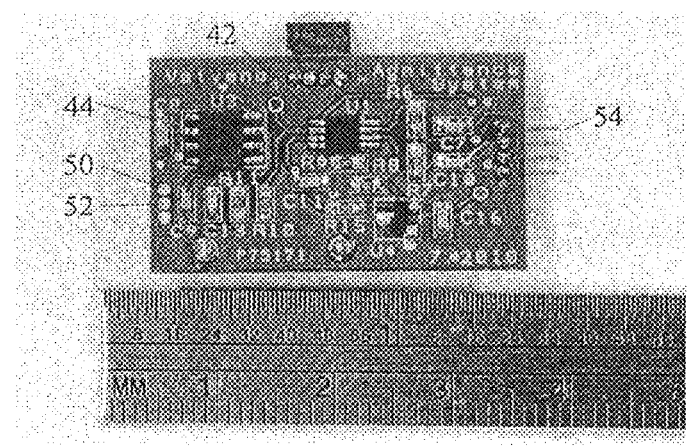
Figure 9A:
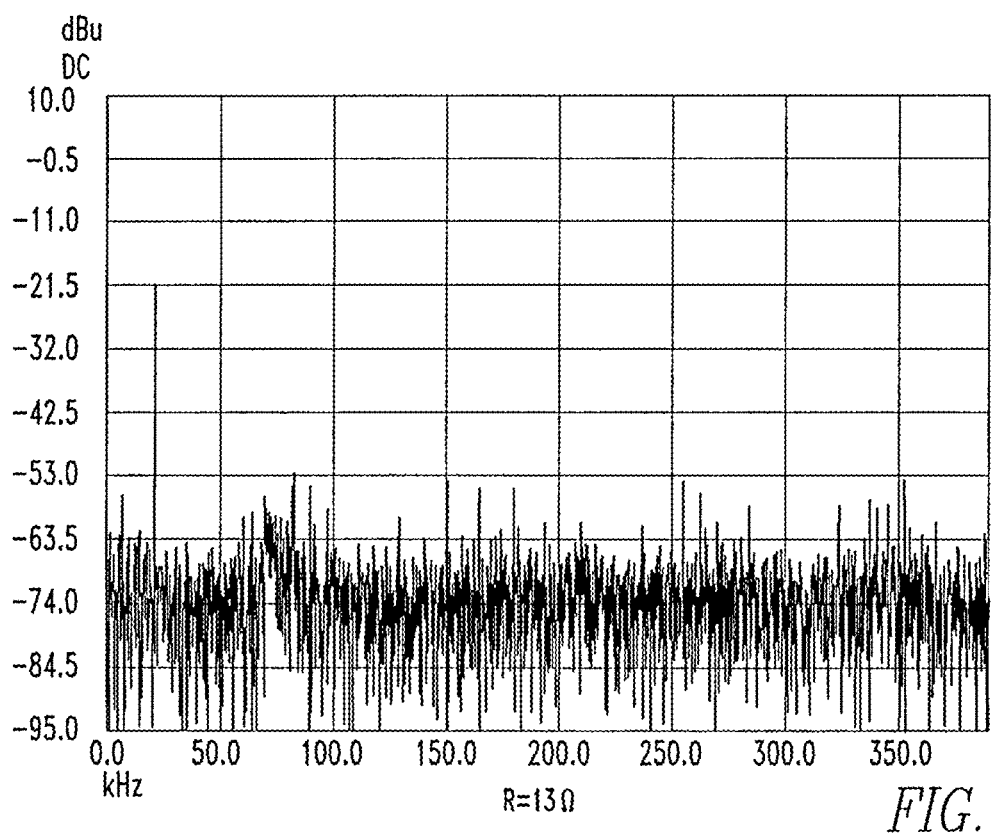
FIGS. 9a-9d show experimental data showing the signal to noise ratio is the equivalent of 10-bits.
Figure 9B:
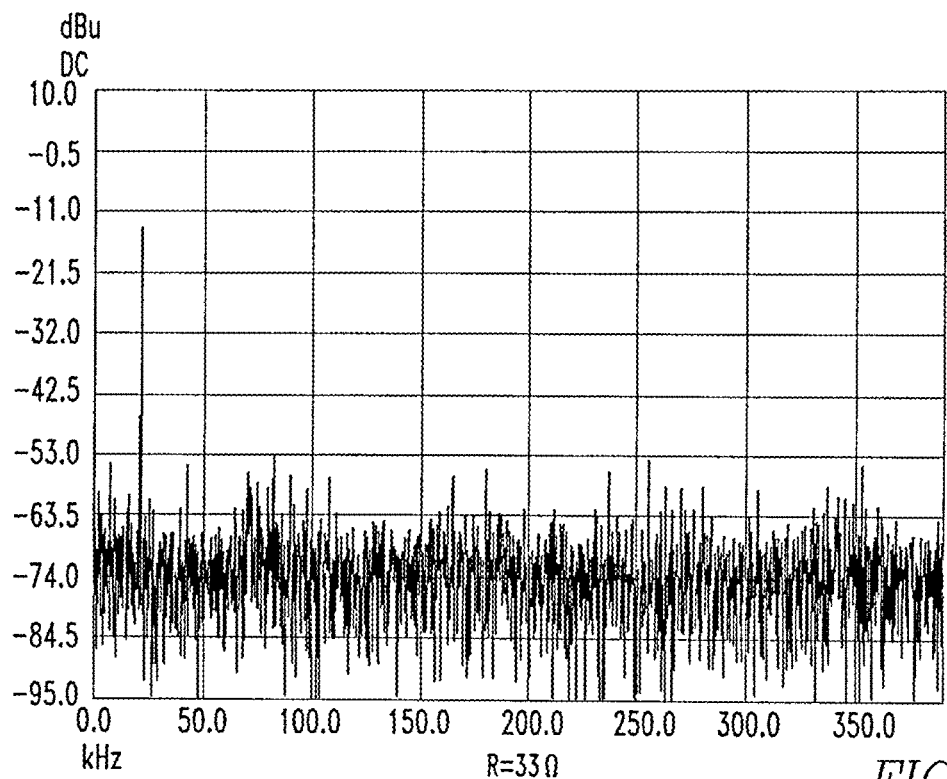
Figure 9C:
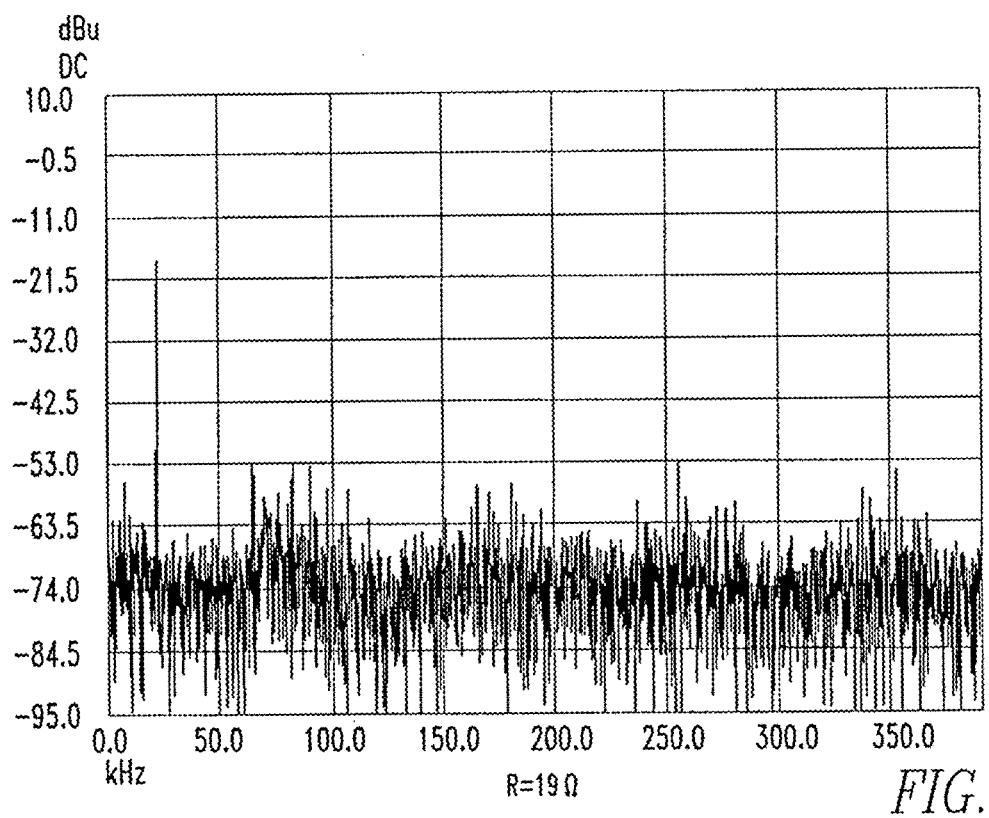
Figure 9D:
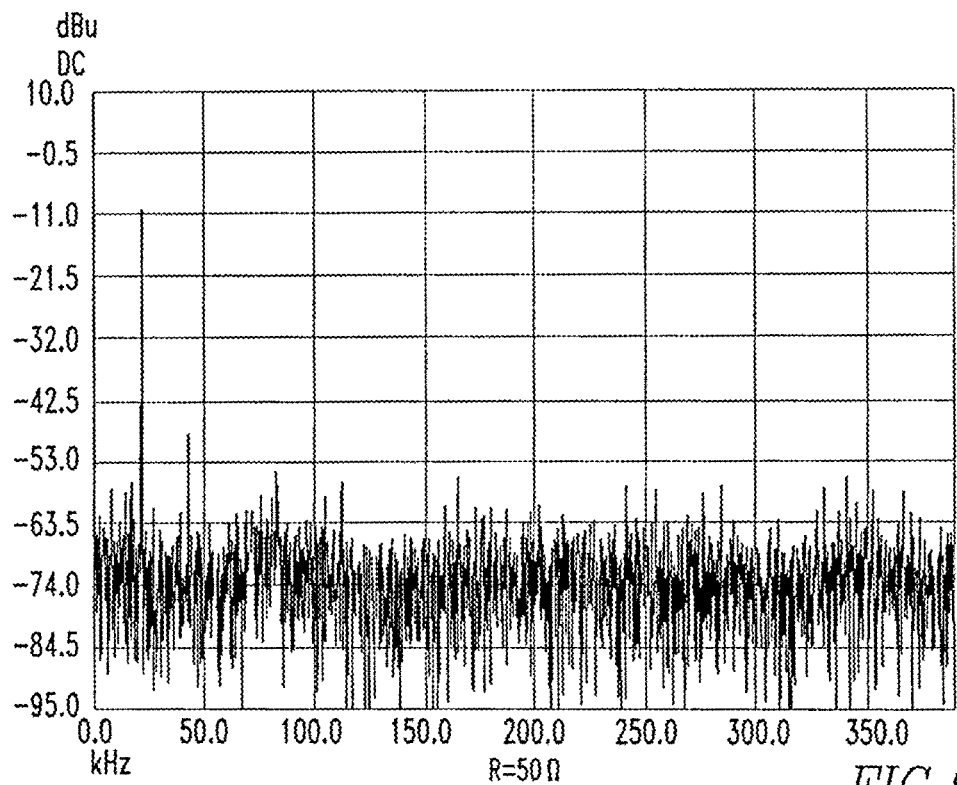

A prototype was built and calibrated as shown in FIGS. 8a and 8b, which implements a 3-bit SinDAC and a 10-bit ADC. FIGS. 9a-9d show the FFT measurements on this system during a continuous sine wave output (not chirped). Signals at 140 kHz and 180 kHz will alias into the 20 kHz bin causing error. Actually, any signal with a frequency of n*160±20 kHz for any integer n will alias, but the 140 and 180 kHz will be the largest source of error. Signal to noise ratio is defined as the ratio of the 20 kHz signal to the 140 kHz and 180 kHz noises. Signals at other frequencies will be removed when calculating the single term of the N-point DFT. The ADC range is 0 to 2.5V, the resolution is 2.5 mV. A 10-bit ADC is the equivalent of 20*log(1/1024)=−60 dB. These data demonstrate the prototype apparatus 100 has a signal to noise ratio of about 10 bits.

When the apparatus 100 is being used to detect heart failure (FIGS. 1a, 1b), the complex impedance (Z=ReZ+jImZ) is sufficient. When the apparatus 100 is being used to measure volume with a lead placed in the heart (FIG. 2), admittance is required. Let Y be the complex admittance (1/Z) at 20 kHz.

Y=Re Y+j Im Y=1/(Re Z+j Im Z)=(Re Z−j Im Z)/(Re $Z^2$+Im $Z^2$)

Re Y=Re Z/(Re $Z^2$+Im $Z^2$)

Im Y=−Im X/(Re $X^2$+Im $Z^2$)

Calculating the value ReZ*ReZ+ImZ*ImZ requires two multiplications, which can be implemented using shift and add. To prevent overflow with finite precision math, the amplitude will be reduced. For example, one possible solution is MagSquare=(Re Z/8)*(Re Z/8)+(Im Z/8)*(Im Z/8)

This calculation is performed with a regular multiplication, e.g., it uses an 8-bit by 8-bit multiplication subroutine. The 65536 in the next equation is a constant to keep the calculations of Y as 16-bit numbers. The units of Y depend on the 65536, the divide by 8 in MagSquare, the instrumentation amp gain, the ADC resolution, and the applied current. They are chosen to make ReY and ImY span the full range of 16-bit signed integers.

Re Y=(65536*Re Z)/MagSquare

Im Y=−(65536*Im Z)/MagSquare

The apparatus 100 is first calibrated using resistors and capacitors of known value. One way to perform a phase calibration is to multiply the impedance signal (or admittance signal) by a complex constant. Let K=$e^{j\theta}$ be a complex constant with magnitude 1, and phase θ. When this is implemented in fixed-point math, it is needed to find three integers {m, $n_1$, $n_2$}, where K=$(n_1+jn_2)/2^m$, such that K has the desired phase, and the magnitude of K is close to 1. Because the system will be calibrated, the magnitude does not have to be exactly equal to 1. For example, K=−1+3j/8 has a magnitude of 1.068 and a phase of 159.7 degrees. To correct for 159.7 degrees of phase in the circuit, multiply Z by K Z*K=(Re Z+j Im Z)*(−1+3j/8)

Re $Z_{corrected}$=−Re Z−3*Im Z/8

Im $Z_{corrected}$=3*Re Z/8−Im Z

A second example of this calibration is, K=1−j/4 has a magnitude of 1.03 and a phase of 345.96 degrees (−14 degrees). To correct for 345.96 degrees of phase, multiply Z by K Z*K=(Re Z+j Im Z)*(1−j/4)

Re $Z_{corrected}$=Re Z+ImZ/4

Im $Z_{corrected}$=−Re Z/4+Im Z

The following table is data showing measured ReY and ImY versus true resistance and conductance. The resistances between lead pins 1-2 and 3-4 were fixed at 499Ω each. Six different 1% metal film resistors were placed between lead pins 2-3, shown as $R_{2-3}$ in FIG. 4. The ReZ ImZ ReY and ImY columns show the average of eight repeated measurements collected by the microcontroller. The standard deviations were calculated from the eight repeated measurements.

| Resistance (Ω) | Conductance (μS) | ReZ | ImZ | ReY | $\sigma_{ReY}$ | ImY | $\sigma_{ImY}$ | \|Z\| | \|Y\| | Phase Y |
|---|---|---|---|---|---|---|---|---|---|---|
| 49.9 | 20040 | 198.8 | −100.9 | 19548.5 | 399.3 | 3956.6 | 1413.8 | 222.9 | 20317.3 | 11.4 |
| 100 | 10000 | 427.9 | −197.1 | 9105.4 | 35.1 | 1720.5 | 29.1 | 471.1 | 9266.5 | 10.7 |
| 200 | 5000 | 883.3 | −290.6 | 4663.0 | 19.5 | 340.5 | 8.5 | 929.8 | 4675.4 | 4.2 |
| 301 | 3322 | 1316.6 | −361.6 | 3174.0 | 10.0 | 73.1 | 2.5 | 1365.4 | 3174.8 | 1.3 |

-continued

| Resistance (Ω) | Conductance (μS) | ReZ | ImZ | ReY | $\sigma_{ReY}$ | ImY | $\sigma_{ImY}$ | \|Z\| | \|Y\| | Phase Y |
|---|---|---|---|---|---|---|---|---|---|---|
| 383 | 2611 | 1629.6 | −415.8 | 2577.3 | 9.3 | 12.6 | 3.3 | 1681.8 | 2577.3 | 0.3 |
| 422 | 2370 | 1782.1 | −448.1 | 2362.1 | 6.0 | 3.5 | 2.3 | 1837.6 | 2362.1 | 0.1 |

Figure 11A:
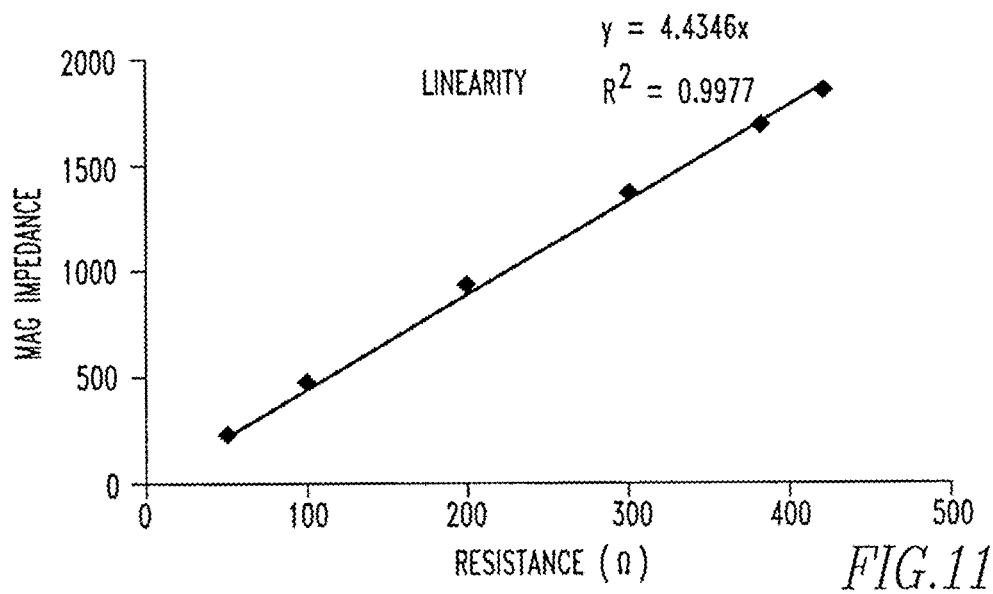
FIGS. 11a, 11b and 11c show experimental data showing the linearity in resistance (11a) and conductance (11b, 11c).
Figure 11B:
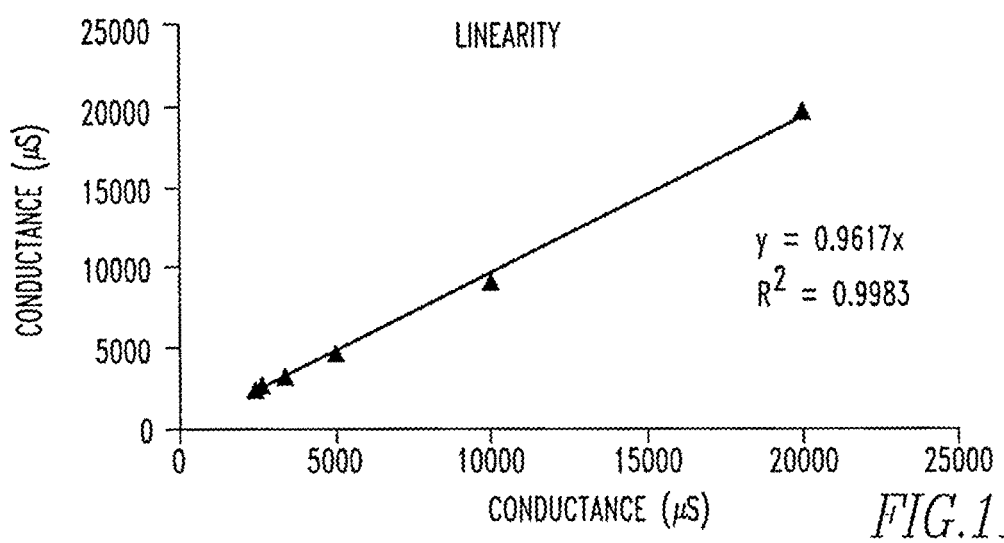
Figure 11C:
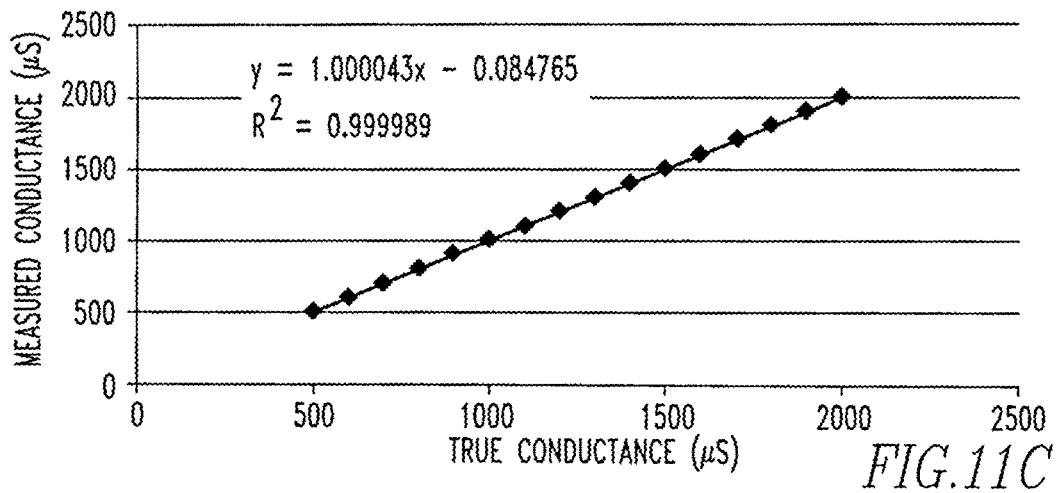
Figure 12A:
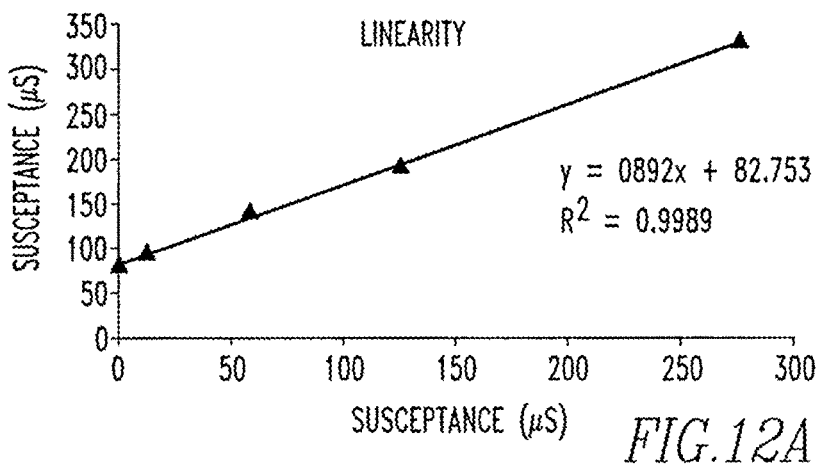
FIGS. 12a and 12b show experimental data showing the linearity in susceptance.
Figure 12B:
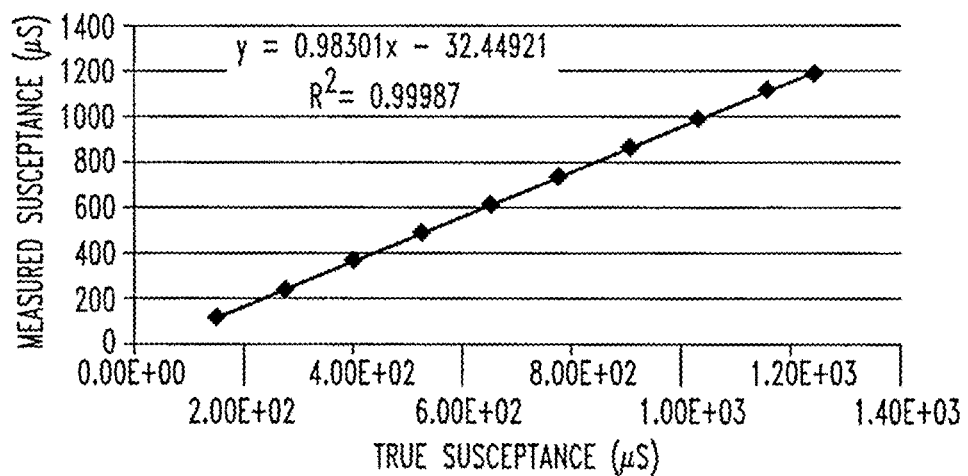

FIGS. 11a-c show the system is linear when measuring impedance and conductance of 1% metal-film resistors. FIG. 12 and the following table show the apparatus 100 is also capable of measuring capacitance (susceptance). The ReY and ImY columns again show the average of eight repeated measurements collected by the microcontroller. The standard deviations were calculated from the eight repeated measurements. The "true" values were measured with a digital multimeter.

| Resistance (Ω) | Conductance (μS) | Capacitance (pF) | Susceptance (μS) | ReY (μS) | $\sigma_{ReY}$ | ImY (μS) | $\sigma_{ImY}$ |
|---|---|---|---|---|---|---|---|
| 301 | 3322 | 0 | 0 | 3274.5 | 9.7 | 79.6 | 3.6 |
| 301 | 3322 | 100 | 13 | 3270.6 | 10.2 | 94.9 | 4.6 |
| 301 | 3322 | 470 | 59 | 3275.8 | 1.8 | 140.4 | 4.8 |
| 301 | 3322 | 1000 | 126 | 3278.6 | 9.7 | 191.9 | 3.3 |
| 301 | 3322 | 2200 | 276 | 3259.9 | 11.9 | 329.6 | 4.1 |
| 301 | 3322 | 4700 | 591 | 3248.8 | 10.3 | 502.1 | 5.6 |
| 301 | 3322 | 10000 | 1257 | 3210.9 | 9.8 | 1136.9 | 5.8 |

Figure 13:
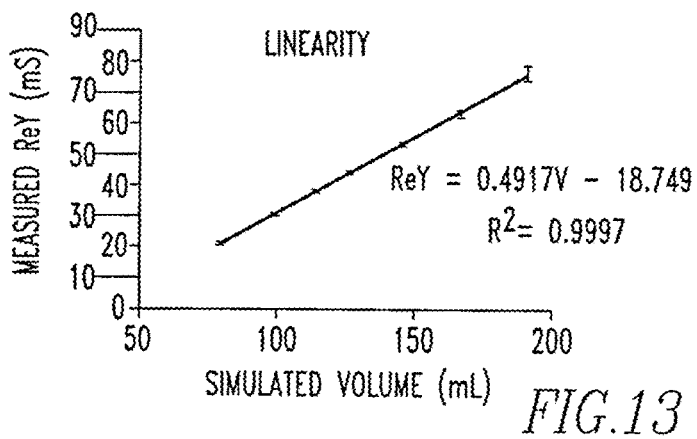
FIG. 13 shows experimental data demonstrating how the apparatus can measure heart volume.

In order to demonstrate how the apparatus 100 can be used to detect heart failure, it was tested with seven precision resistors. The simulated LV volume, V, is defined as 2G+40 (this matches experimental data obtained in pigs). The "true" resistance values were measured with a 3.5 digit DVM. Admittance was measured 8 times at 10 Hz with a 12-cycle chirp, and the standard deviation a is based on these repeated measurements (FIG. 13).

| R(ohm) | G (mS) | V(mL) | ReY (mS) | $\sigma_{ReY}$ | ImY | YPhase | \|Y\| | \|Z\| |
|---|---|---|---|---|---|---|---|---|
| 13.17 | 75.93 | 191.86 | 75.98 | 2.13 | 11.35 | 8.49 | 76.82 | 364.48 |
| 15.68 | 63.78 | 167.55 | 62.97 | 1.21 | 7.33 | 6.64 | 63.40 | 435.66 |
| 18.94 | 52.80 | 145.60 | 52.99 | 0.37 | 4.57 | 4.92 | 53.19 | 516.36 |
| 23.05 | 43.38 | 126.77 | 43.68 | 0.36 | 2.61 | 3.42 | 43.76 | 618.56 |
| 26.88 | 37.20 | 114.40 | 37.39 | 0.45 | 1.65 | 2.53 | 37.43 | 716.19 |
| 33.89 | 29.51 | 99.01 | 30.00 | 0.21 | 0.82 | 1.57 | 30.01 | 908.55 |
| 50.45 | 19.82 | 79.64 | 20.44 | 0.11 | 0.31 | 0.88 | 20.44 | 1324.50 |

A saline calibration is used to remove the imaginary part due to the circuit or the lead. The system will be calibrated in saline to get a relationship between ReY and ImY. Let $f$ be the functional relationship between ImY=$f$(ReY) in saline, representing the response of the lead. This might be a simple constant, a linear fit or a table lookup with interpolation. $C_m$ is the muscle capacitance, and $G_m$ is the muscle conductance. In saline, the calculation of $C_m$ should be zero. However, in vivo $C_m$ will represent the capacitance of the tissue.

$$C_m = (\text{Im } Y - f(\text{Re } Y))/(2\pi 20 \text{ Hz})$$

The constant SigEplRatio is standard σ/ε ratio $$G_m = \text{SigEplRatio} * C_m$$

$$G_b = \text{Re } Y - G_m$$

The blood conductance ($G_b$) is used to derive heart volume using the equations developed in prior art.

Figure 14:
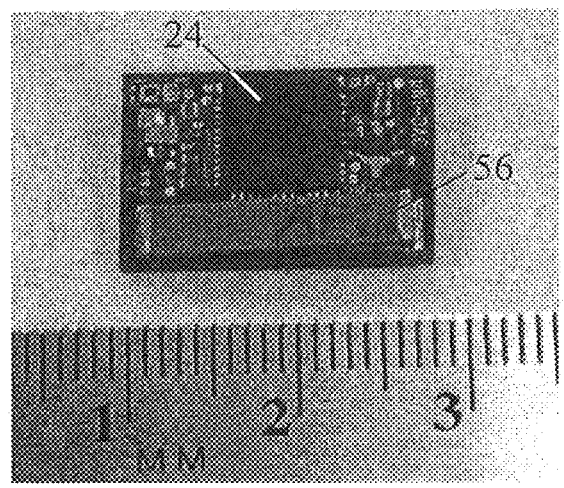
FIG. 14 is a photograph of the wireless version of the prototype.
Figure 15:
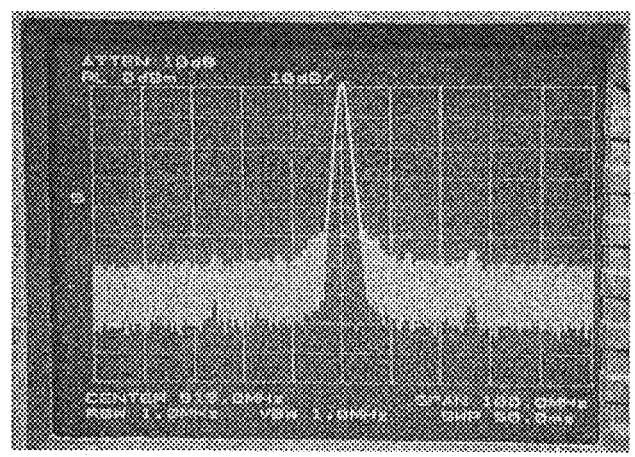
FIG. 15 shows experimental data showing the wireless data as transmitted by the apparatus.

One option for the apparatus 100 is to implant it in animals. FIG. 2 shows the animal system with an admittance-pressure lead in a ventricle. FIG. 5 shows the block diagram of this configuration. The admittance channel is the same as previously described. This apparatus 100 has a pressure sensor (41), amplifier (43) and filter (45). The communication link implements wireless communication (52). FIG. 14 shows the wireless version of the apparatus 100. The antenna (56) transmits data, and a receiver connected to a computer receives the data. This way, pressure-volume loops are recorded in real time.

Figure 16:
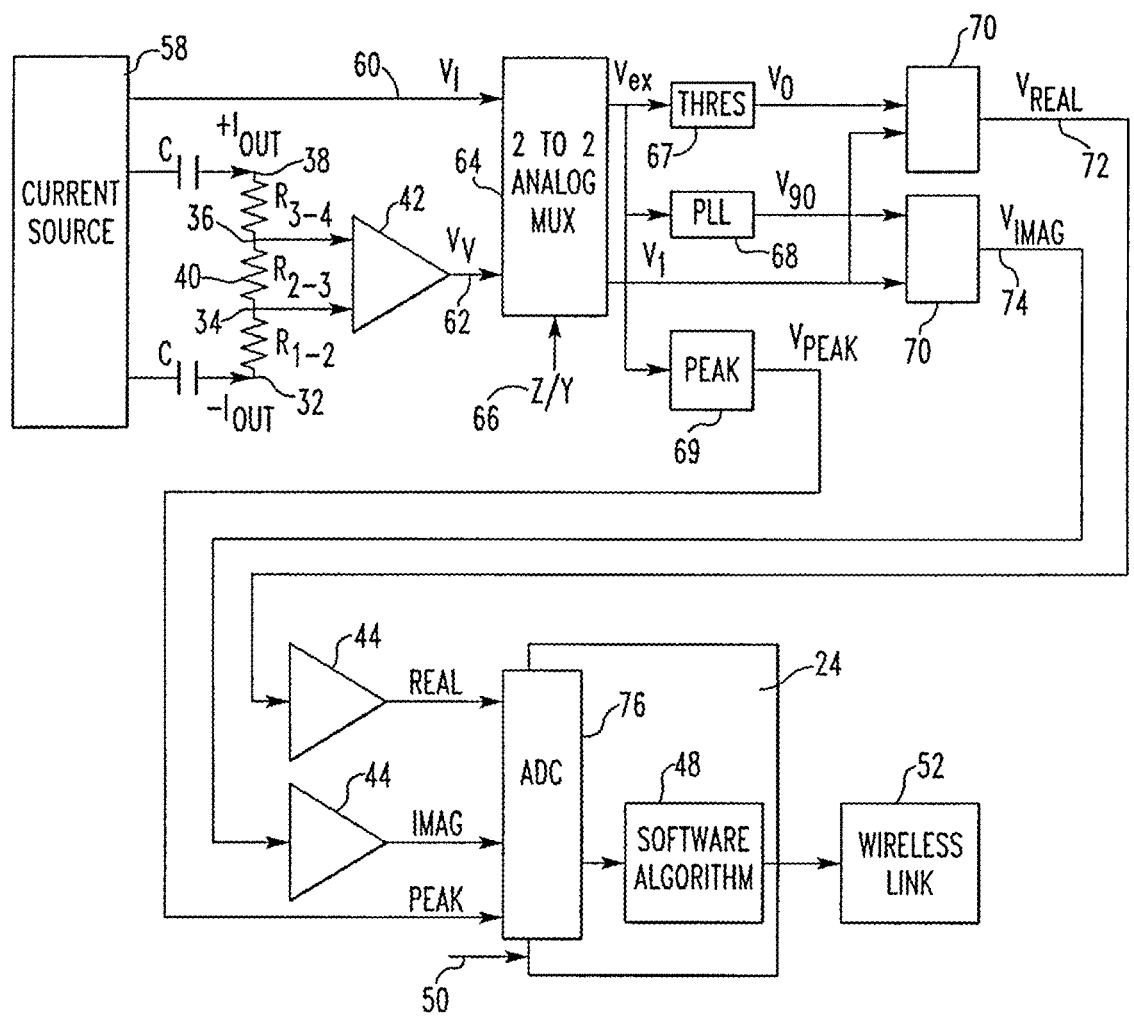
FIG. 16 is a block diagram of the apparatus using a synchronous demodulator with four-quadrant mixers.
Figure 17:
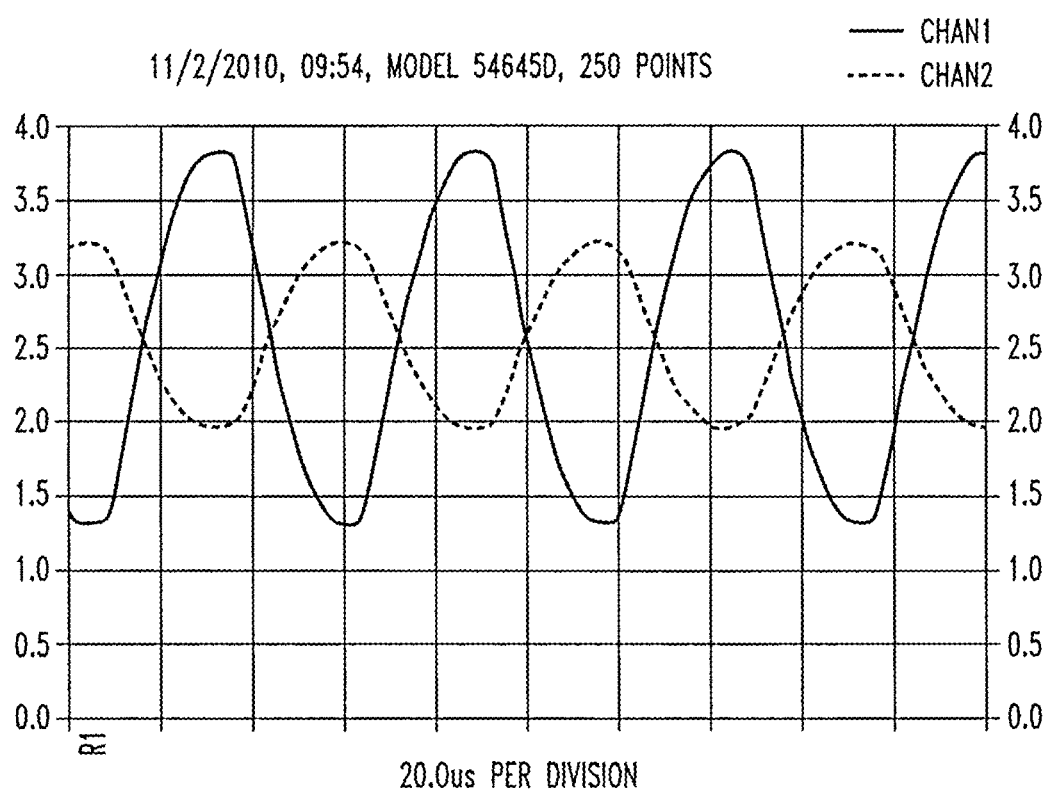
FIG. 17 shows voltage across 100 ohm $R_{2-3}$ resistor (CH2) and current waveforms (CH1) measured with the synchronous demodulator version.

There is an alternative low power technique to measure complex electrical properties using a synchronous demodulator, as shown in FIG. 16. This method can be configured to measure either impedance or admittance. The method begins with an AC current source (58). The frequency of this source will determine the frequency at which the electrical properties are measured. Similar to the other techniques, the current is applied across electrodes 1 (32) and 4 (38). $V_I$ (60) is an AC voltage signal that has an amplitude and phase matching the applied current. Also similar to the other techniques, the resulting voltage across electrodes 2 (34) and 3 (36) is measured with an amplifier (42). $V_V$(62) is an AC voltage signal that has an amplitude and phase matching the voltage between electrodes 2 and 3. Because the transducer is excited with a constant current, this signal represents the complex impedance, Z=ReZ+ jImZ. There is a digital signal (66) that controls a 2-input 2-output analog switch (64). A peak detector (69) on the signal VEX can be added to assist in calibrating the measurement.

When the apparatus 100 is configured in impedance mode, the analog switch (64) makes $\{V_1=V_V, V_{EX}=V_I\}$. The threshold detector (67) creates a digital square wave, $V_0$, which is in phase with $V_I$. The phase lock loop, or PLL, (68)

creates a digital square wave, $V_{90}$, which is 90 degrees out of phase with $V_I$. Two four-quadrant mixers (70) are used to separate the real and imaginary parts of impedance Z. The voltages $V_{real}$(72) and $V_{imag}$(74) are DC signals representing ReZ and ImZ respectively.

When the apparatus 100 is configured in admittance mode, the analog switch (64) makes $\{V_{EX}=V_V, V_1=V_I\}$. The threshold detector (67) creates a digital square wave, $V_0$, which is in phase with $V_V$. The PLL, (68) creates a digital square wave, $V_{90}$, which is 90 degrees out of phase with $V_V$. In this configuration, the two synchronous demodulators (70) are used to separate the real and imaginary parts of admittance Y. In this mode, the voltages $V_{real}$(72) and $V_{imag}$(74) are DC signals representing ReY and ImY respectively.

Because $V_{real}$(72) and $V_{imag}$(74) are DC signals, they can be sampled with a low power ADC (76) at frequencies determined by the change in heart volume. For example, if the heart rate is 1 beat per second, or 60 BPM, 100 volume measurements per beat can be created by sampling the ADC at 100 Hz. The phase correction, calibration and determination of heart volume are identical to other techniques developed by many of the inventors in pending patent applications (see the list of references below). A board level apparatus 100 was built and calibrated. The following data shows the technique is capable of measuring complex electrical properties. Although using a synchronous demodulator has been used previously to measure complex electrical properties, this apparatus 100 can be easily configured to directly measure either impedance or admittance.

| R(Ω) | C(nF) | $V_{real}$(V) | $V_{imag}$(V) | ReZ(Ω) | ImZ(Ω) | C(nF) |
|---|---|---|---|---|---|---|
| 50 | 0 | 0.2127 | −0.0142 | 53.3 | 0 | 0 |
| 50 | 10 | 0.2127 | −0.0235 | 53.5 | 1233.7 | 7.2 |
| 50 | 20 | 0.2105 | −0.0325 | 53.4 | 616.2 | 14.3 |
| 50 | 30 | 0.2071 | −0.0438 | 53.5 | 374.6 | 23.6 |
| 100 | 0 | 0.4225 | −0.0268 | 106.0 | 0 | 0 |
| 100 | 10 | 0.4226 | −0.0632 | 108.0 | 1256.8 | 7.0 |
| 100 | 20 | 0.4042 | −0.097 | 106.9 | 606.5 | 14.6 |
| 100 | 30 | 0.3872 | −0.1333 | 108.3 | 386.3 | 22.9 |

Example: One embodiment is now presented, which is believed to be the preferred technique herein at this time to measure heart volume optimizing for size and power. The four-electrode lead (32, 34, 36, and 38) is placed in either of the two configurations shown in FIGS. 1a and 1b. A 20 kHz sine wave current (30) is applied across electrodes 1 (32) and 4 (38) for 400 μsec, and the resulting voltage measured between electrodes 2 (34) and 3 (36) is amplified (42). The 400 μsec chirp (FIG. 3) is sampled by the ADC (46) at 160 kHz and software calculates LV volume from the digitized samples. Typical inputs to the ADC are shown in FIG. 3. One measurement requires 440 μsec, after which the system enters a low-power sleep mode. In this system, LV volume will be measured 50 times each hour. The largest volume measured each hour is assumed to be the end-diastolic volume, which is output using a synchronous serial port of the microcontroller. Therefore, the system is powered for only 4.4 ms each hour.

Figure 18:
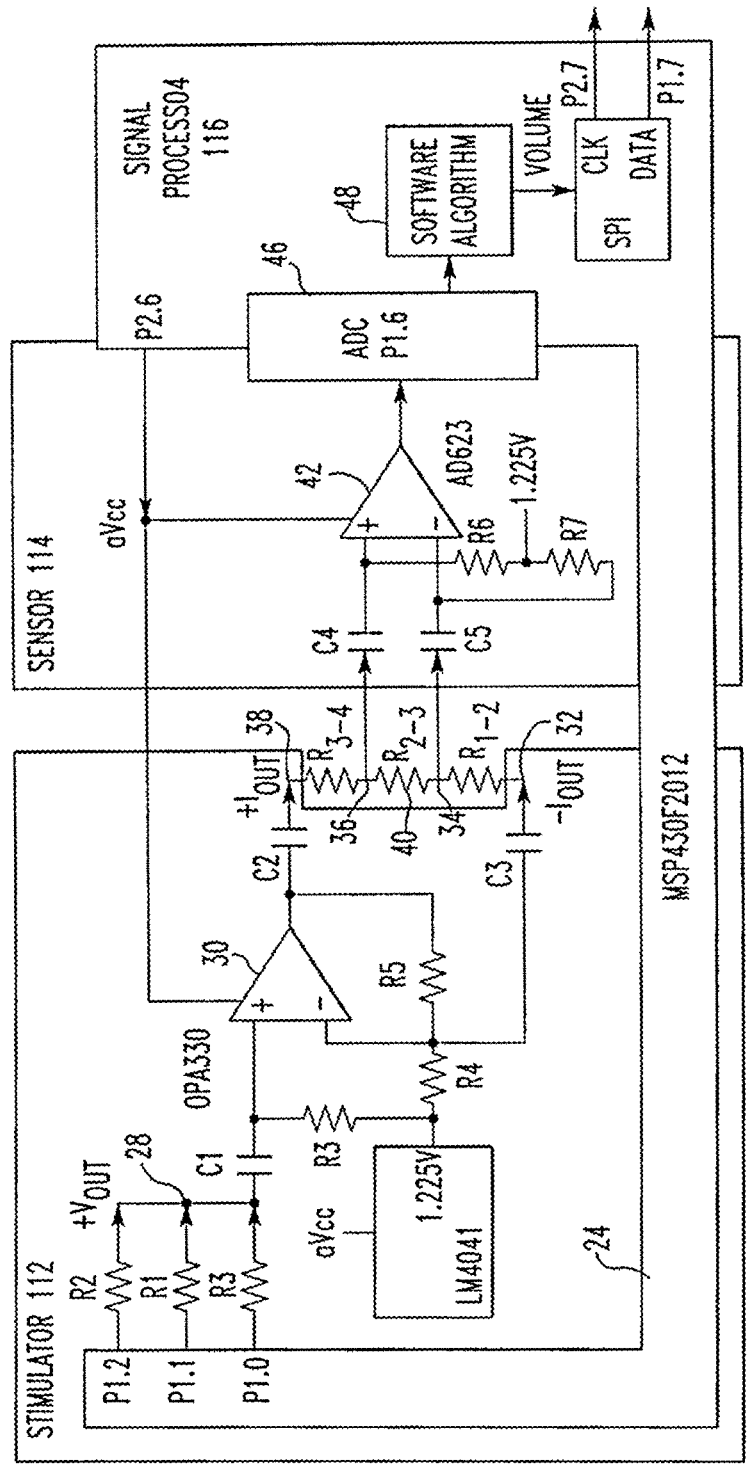
FIG. 18 shows an electronic circuit that can be used to measure heart volume.

In this paragraph, the hardware details will be presented, as shown in FIG. 18. The microcontroller (24) is an MSP430F2012, powered at 3.3 V, running at 16 MHz. This apparatus 100 was chosen because of its low power. The system requires 2 k ROM, 128 bytes of RAM, 6 digital outputs, and one analog input. The microcontroller output P2.6 is used to power the analog circuit. When P2.6 is low, the analog circuit is off, drawing no current. When P2.6 is high (3.3V), the analog circuit is active. The system uses one 3-bit SinDAC (24), with R2=147 kΩ, R1=205 kΩ, and R0=499 kΩ. More bits in the SinDAC would give a better sine wave, but 3 bits represent a good tradeoff between accuracy and size. The important parameter when designing a SinDAC is the number of output per cycle. If one were to increase the number to 16, then the microcontroller would need to run twice as fast, requiring more power to operate. In this system there are 8 outputs per cycle, and this was chosen to balance measurement accuracy and low power. The digital output pattern is 3,6,7,6,3,1,0,1. This means the 3-bit binary outputs from the MSP430F2012 (shown as P1.2, P1.1, P1.0 in FIG. 18) will be the sequence: 011, 110, 111, 110, 011, 001, 000, 001, which is output at 160 kHz. The values of R2, R1, R0 were found by minimizing the mean squared error between the desired sine wave shape and $V_{out}$, given the constraint that the resistors must be E-96 standard values larger than 100 kΩ. The capacitor shown in FIG. 3 is optional, and has been left off in this system to save space. The OPA330AIDCKT op amp (30) is used to convert the SinDAC voltage to current. The op amp is chosen because of its low power and low noise. The capacitor C1 is 2.2 nF, chosen to pass 20 kHz and reject DC. The 1.225 V reference (created with LM4041A12IDCKR) creates a DC offset in the analog circuits, so the entire analog circuit will run off one 3.3V power supply. R3 is 25.5 kΩ, and it is used to reduce the AC amplitude out of the SinDAC to 0.3V rms. R4 is 4.99 kΩ, and it is used to set the applied current across electrodes 1 and 4 to 60 μA rms. C2 and C3 are both 0.1 μF, and their purpose is to prevent DC current from passing across the electrodes. DC current must be removed so the system will exhibit long-term stability. Again the values of C2 and C3 are chosen to pass 20 kHz and block DC. The resistors labeled $R_{34}$, $R_{2-3}$ and $R_{2-1}$ in FIG. 19 do not represent resistors in the circuit, but rather they represent impedances in the heart itself. In particular, $R_{34}$ means the heart impedance between electrodes 3 and 4; $R_{2-3}$ means the heart impedance between electrodes 2 and 3; and $R_{2-1}$ means the heart impedance between electrodes 1 and 2. The heart volume is derived from the blood component measured in $R_{2-3}$. C4 and C5 are 0.01 μF. Similar to C2 and C3, C4 and C5 are used to pass AC signals and block DC current. Resistors R6 and R7 are 100 kΩ, and provide 1.225 V offset to the inputs of the instrumentation amp (42). The AD623ARM instrumentation amp (42) provides a gain of 101. The AD623 was chosen for its CMRR at 20 kHz, and its low power. The 101 gain essentially defines the impedance range of the system. With the 60 μA rms current and gain of 101, the measurement range of impedance is 10 to 150Ω. This range allows measurements in humans, dogs and pigs with the either electrode configuration shown in FIGS. 1a, 1b. One could add an analog low pass filter (44) between the instrumentation amp (42) and the ADC (46). The purpose of the filter would be to pass 20 kHz and reject 140 and 180 kHz. The measurements are just a little bit noisier without the filter. So, in this system the filter was not included to save power and space. The 10-bit ADC is sampled at 160 kHz, synchronized to the 160 kHz digital output to the SinDAC.

Figure 19A:
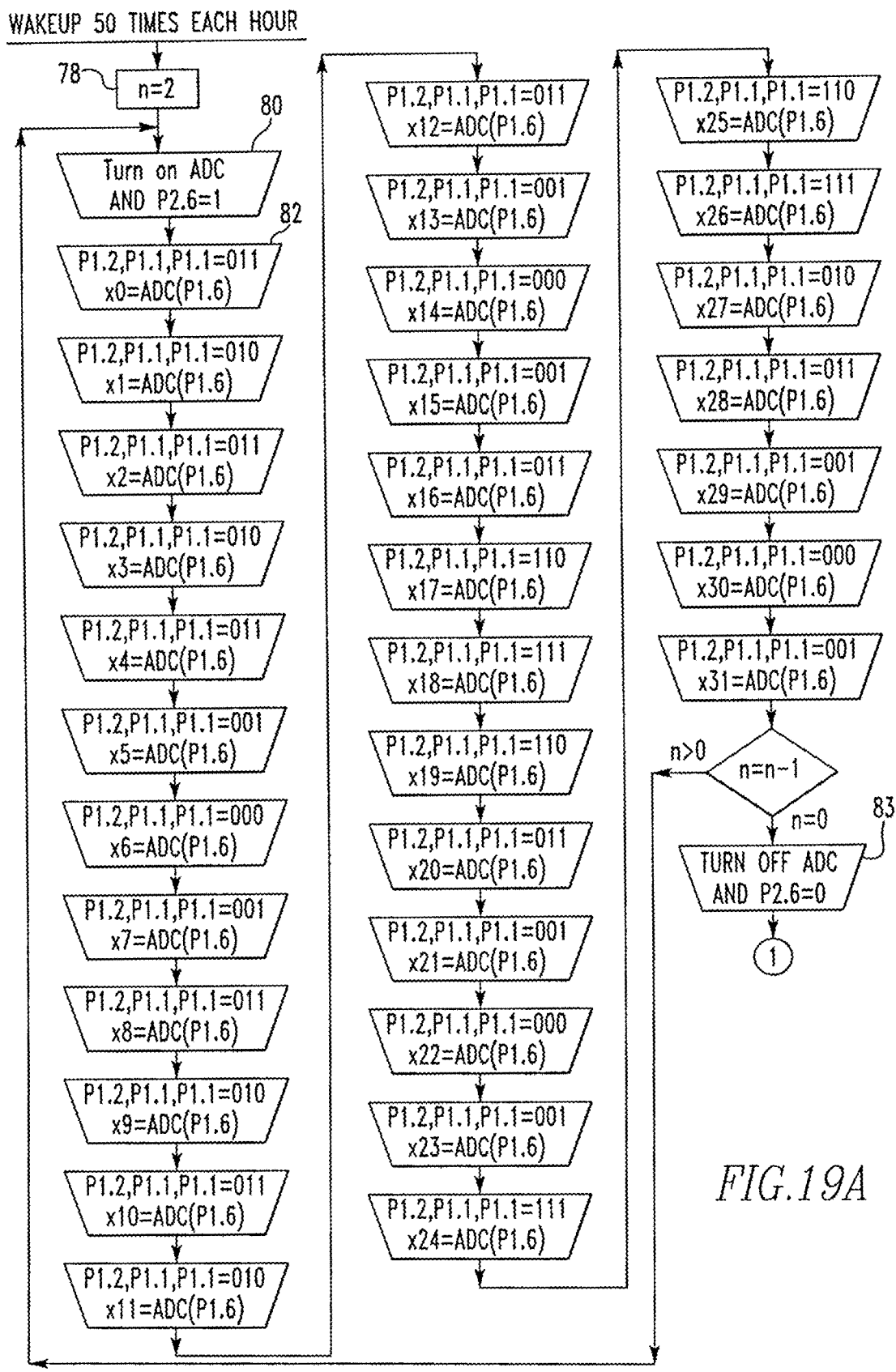
FIG. 19a is a flow chart of software used to create output and sample input.
Figure 19B:
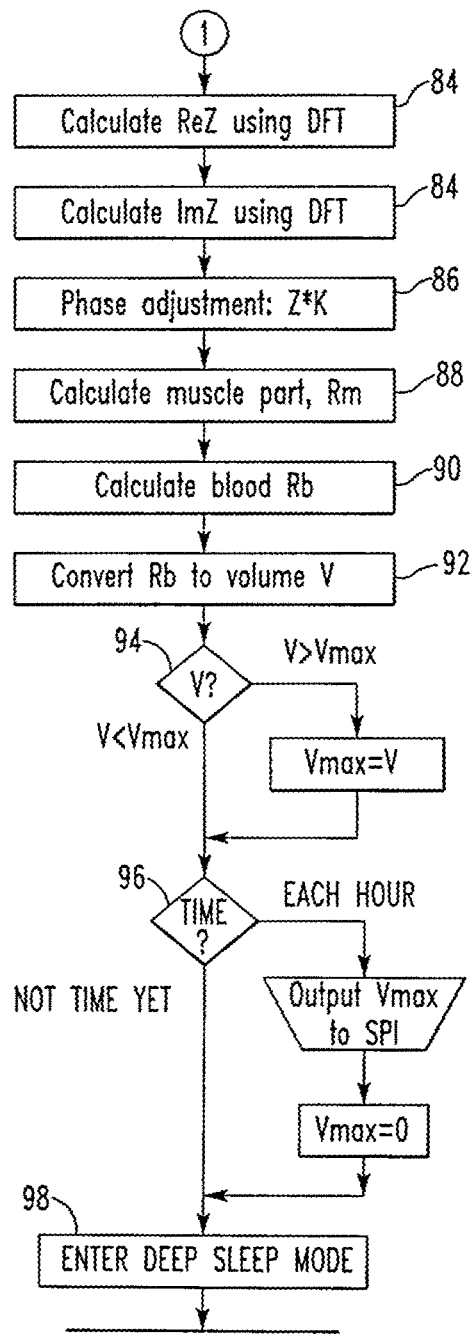
FIG. 19b is a flow chart of software used to measurements into volume.

In this paragraph, the software details will be presented, as shown in FIG. 19. Fifty times an hour, the system awakes from deep sleep using a timer built into the MSP430. A counter, n, is set to 2 (78), which determines the length of the chirp length. Next, the ADC and analog circuits are turned on (80). To save space and lower power, the actual microcontroller output P2.6 serves as the analog power input for the three analog chips, labeled as aVcc in FIG. 18. For each n, there will be 32 SinDAC outputs and 32 ADC inputs (82). Since there are 8 outputs per cycle in the sine wave, 64 outputs means there will be 8 sine wave cycles. Since the output/input pairs occur at 160 kHz, the chirp lasts 400 μsec. The system records the last 32 ADC inputs in the variables $x_0$ to $x_{31}$. After the data are collected, the ADC and analog circuit is powered down (83). Next, the 32-point DFT is calculated on collected data $x_0$ to $x_{31}$ (84).

$$\text{Re } Z = (17*(x_0 - x_4 + x_8 - x_{12} + x_{16} - x_{20} + x_{24} - x_{28}) + 12*(x_1 - x_3 - x_5 + x_7 + x_9 - x_{11} - x_{13} + x_{15} + x_{17} - x_{19} - x_{21} + x_{23} + x_{25} - x_{27} - x_{29} + x_{31}))/32$$

$$\text{Im } Z = (17*(-x_2 + x_6 - x_{10} + x_{14} - x_{18} + x_{22} - x_{26} + x_{30}) + 12*(-x_1 - x_3 + x_5 + x_7 - x_9 - x_{11} + x_{13} + x_{15} - x_{17} x_{19} + x_{21} + x_{23} - x_{25} - x_{27} + x_{29} + x_{31}))/32$$

To save power, a microcontroller without hardware multiply/divide was used. Multiply by constants are implemented with shifts and adds. For example, A=17*B is calculated as A=(B<<4)+B. Similarly, A=12*B is calculated as A=(B<<3)+(B<<2). The divide by 32 is implemented as a right shift. The lead is calibrated in saline, where no imaginary part is expected (i.e., ImZ should be zero). To correct for phase shift in the circuit and lead, the input is multiplied by a complex constant K (86). This system required a correction of −16 degrees, and uses a K equal to ⅞−j/4, which has a magnitude of 0.91 and a phase of 344.05. To correct for phase, multiply Z by K $$Z*K = (\text{Re } Z + j \text{ Im } Z)*(⅞ - j/4)$$

$$\text{Re } Z_{corrected} = 7*\text{Re } Z/8 + \text{Im } Z/4$$

$$\text{Im } Z_{corrected} = -\text{Re } Z/4 + 7*\text{Im } Z/8$$

Again, the multiply by 7 was implemented as a series of shifts and adds. The σ/ε ratio is a muscle property constant, relating muscle resistance to capacitance.

$$\varepsilon_m / \sigma_m = R_m * C_m$$

A series R-C model is used to convert ImZ to the impedance of the muscle, $R_m$ [31]. ω is equal to 2 times π times 20 kHz.

$$R_m = \frac{-\text{Im} Z * \left(1 + \left(\frac{\omega \varepsilon_m}{\sigma_m}\right)^2\right)}{\frac{\omega \varepsilon_m}{\sigma_m}}$$

The blood resistance, $R_b$, is calculated by subtracting off the muscle component (90) [31].

$$R_b = \text{Re} Z - \frac{R_m}{1 + (\omega R_m C_m)^2} = \text{Re} Z + \text{Im} Z * \frac{\sigma_m}{\omega \varepsilon_m}$$

The software performs this calculation using fixed point math.

$$R_b = \text{Re } Z + (c*\text{Im } Z)/2^m$$

where c and m are integers, such that $c/2^m$ approximates σ/εω. If desired, the blood conductance is inversely related to impedance, $G_b = 1/R_b$. The $R_b$ and $G_b$ measurements can be used as a relative measure of volume. For example, $R_b$ could be used to optimize a pacemaker timing or used to detect impending heart failure.

The relationship between blood resistance $R_b$ and volume V (92) is nonlinear. If desired, the apparatus 100 uses either piece-wise linear fit or a parametric equation to quantify volume. This relation is calibrated in vivo using known volumes.

The maximum volume over the last hour is saved in Vmax (94). Once an hour this measurement is output to other modules in the system using a synchronous serial protocol (96). 49 times out of 50, the active mode functions require 440 μs. Every 50th activation, the synchronous serial output requires an additional 20 μs.

Power was measured with the apparatus 100 with $f_s$ equal to 20 kHz and a chirp rate set at 10 Hz. This system just measured volume (no pressure measurements or wireless communication.) When in active mode, the system requires an average of 6.6 mA. Active mode runs for 440 μs every 100 ms while chirping. To save power, all analog electronics is turned off while sleeping. In sleep mode with periodic wakeup, the system required 0.5 μA. FIGS. 10a and 10b plot the analog power supply voltage showing the chirp occurring every 100 ms. With 8 cycles/chirp, the analog power is applied for 400 μs, which is 0.4% of the time. It takes about 40 μs to perform the software calculations, so the apparatus 100 is active 0.44% of the time. This is an average of about 45 μA. If a chirp for 5 seconds occurs once an hour (50 volume measurements an hour), the average current drops to less than 1 μA.

6.6 mA*440μs/100 ms*50chirps/hr*1 hr/3600 sec+ 0.5μA=0.9μA

TABLE 1

Comparison to prior art
Sunagawa [32] made a portable system for rats using dual frequency
Raghavan [33-34] made a portable system for rats using admittance
Best practice, in terms of what has been actually built and is operative for the technique described herein of the present invention without wireless or pressure.
Best practice in terms of what has been actually built and is operative for the technique described herein of the present invention with wireless and pressure.

|  | Sunagawa | Raghavan | Best | Best + wireless + pressure |
|---|---|---|---|---|
| Current while sampling |  | 42 mA | 6.6 mA | 5 mA |
| Average current |  | 24 mA | 0.9 μA | 60 μA |
| Average power = current * 3.6 V |  | 86 mW | 3.2 μW | 216 μW |
| Size (wo battery, lead) | 11 mL | 14 mL | 1.0 mL | 2.3 mL |
| Weight (wo battery, lead) | 14 g | 9 g | 1.3 g | 2.6 g |

The technique applies a sinusoidal current at one specific frequency, f. This current does not stimulate the tissue. The apparatus 100 uses one or more SinDACs to create sine waves at frequency f. When using multiple SinDACs, the phase between the waves can be precisely controlled. E.g., a phase of 0, 90, 120, 180, 240, or 270 degrees can easily be achieved. The apparatus 100 uses software to create chirped stimulations, resulting in very low-power operation compared to the now-standard continuous wave embodiments. FIG. 3 shows experimental recordings at the ADC input made with the apparatus 100, showing the dependence on load resistance (blood volume) and the chirped sinusoid. Setting the frequency involves a single software parameter, which is easy to change. The experimental data presented here was obtained at f=20 kHz, but the method will work for any frequency below 100 kHz and is limited only by the speed of existing off-the-shelf low-power microcontrollers and analog electronics. Using the software algorithm with the hardware SinDAC removes the crystal oscillator and high-Q frequency-select analog filter required by previous systems.

There is software synchronization of sine wave output generated by the SinDAC and the ADC sampling input. This synchronization provides for accurate measurements of the phase between current output and voltage input. DAC outputs and ADC inputs are triggered by the same software and occur at an integer multiple (M) of f. The accurate measurement of phase means the system is capable of distinguishing between the real and imaginary parts of the electrical property measurement. To reduce power, M is selected to be a power of 2. I.e., $M=2^m$, where m is a positive integer. For example, if M=8, there are 8 DAC outputs and 8 ADC samples per sinusoid period. However, the approach will work for any integer M (e.g., there is an M=12 example shown later.)

The apparatus 100 calculates one term of an N-point DFT. To reduce power, N is also selected to be a power of 2. I.e., $N=2^n$, where n is a positive integer greater than or equal to m. This allows for a simple calculation of the real part of impedance and imaginary part of impedance at one specific frequency (f), without having to measure magnitude and phase. Power is saved by performing these calculations in software, rather than using analog electronics to create the output signal. However, the approach will work for any integer N (e.g., there is an N=24 example shown earlier in paragraph 107.)

The apparatus 100 measures the real and imaginary parts of impedance directly. If needed, the real and imaginary parts of admittance are calculated by inverting impedance in software. This calculation eliminates the analog divider found in previous systems, thus reducing power. Furthermore, the apparatus 100 does not actually measure magnitude or phase, because the real and imaginary parts are sufficient to derive cardiac volumes. This approach removes the rectifier and phase detection analog hardware found in all previous systems. When detecting heart failure and when optimizing pacemaker timing, only the real and imaginary parts of impedance are needed. When measuring heart volume with a lead inside the ventricle, the real and imaginary parts of admittance are required. The fact that the new embodiment apparatus 100 measures the needed parameters directly removes the necessity to perform power-expensive trigonometric calculations (e.g., sine, cosine, and arctan), found in existing apparatuses.

The microcontroller can turn on the analog power for the analog subsystem to perform the measurement, and it can turn off the power when the analog subsystem is not needed. More specifically, a digital output of the microcontroller serves as the analog power signal. This means the analog circuit requires no current at all while in sleep mode. Furthermore, the microcontroller can put itself into low-power sleep mode, such that the entire system requires much less than 1 μA while sleeping. If fifty volume measurements are made every hour, the prototype apparatus 100 will run using a time-average current less than 1 μA.

There are two trigger modes to awake the apparatus 100 from sleep. First, the apparatus 100 can be programmed to awake periodically (e.g., once an hour). Second, a digital input pin (50) can be used to awake the system. For example, if there is an ECG, then this trigger can be configured to sample heart volume at end diastole.

Although the DFT is a complex algorithm usually requiring significant processing power, an implementation has been developed that calculates a single point of an N-point DFT using extremely modest computer processing power. The implementation needs only 16-bit addition, subtraction, and shift operations. If N is chosen to be 32, as one example, then the method requires only 128 bytes of RAM. In particular, no hardware support for multiply, divide, or floating point calculation is required. Although the initial prototype was implemented using an MSP430 (see FIGS. 8 and 14), the algorithm can run on any microcontroller with digital outputs and an analog input. It can even be implemented in digital logic. This simplicity makes it much easier to embed into existing pacemaker apparatuses. The software runs in real time, and the results can be output in serial fashion.

An alternate implementation of the measurement has been built and tested using a synchronous demodulation technique (FIG. 16). The circuit creates separate analog signals representing the real part and imaginary parts of admittance, using two four-quadrant mixers (70) to extract the in-phase and in-quadrature components of the measured signal. Using an analog switch (64), it can be configured to create analog signals representing either impedance or admittance. The advantage of this approach is the ADC is sampled only twice per measurement. Although the synchronous demodulation technique is a standard approach for capacitance measurement, the apparatus 100 operates at low power.

DRAWINGS—REFERENCE NUMERALS

10—Four electrodes for admittance measurement, located in the ventricle
12—A single lead placed in the ventricle
14—The apparatus can be added to or embedded into existing apparatuses, such as a pacemaker
16—The system can communicate with the patient or medical staff through a transmitter
18—Electrodes 1 and 2 placed on the heart (in a coronary vein)
20—Electrodes 3 and 4 placed in the heart (in a ventricle or atrium)
22—Paths as current flows between electrodes 1 and 4
24—Microcontroller or digital logic
26—Digital outputs synchronized (controlled) by software
28—One or more SinDACs used to create a sine wave at a specific frequency
30—Voltage to current circuit applying current to electrodes 1 and 4
32—Electrode 1, current stimulation
34—Electrode 2, voltage sensing
36—Electrode 3, voltage sensing
38—Electrode 4, current stimulation
40—Resistance $R_{2-3}$ represents the resistance from the blood volume in the heart
41—Pressure sensor (optional)
42—Low power amplifier
43—Low power amplifier for the pressure channel (optional)
44—Low power analog filter (optional)
45—Low power analog filter for the pressure channel (optional)
46—ADC with sampling synchronized to SinDAC outputs
48—Software algorithm to measure heart volume from electrical property measurements
50—Possible external trigger input to wake up the apparatus 52—Digital link to other system components, for example a wireless link
54—4-wire connector to electrode
56—Antenna used to send wireless communication
58—AC current source driving electrodes 1 and 4 with a constant current
60—AC voltage ($V_I$) with amplitude and phase related to the applied current applied to electrodes 1 and 4
62—AC voltage ($V_V$) with amplitude and phase related to the resulting voltage measured between electrodes 2 and 3
64—Analog switch connecting either {$V_{EX}=V_V$, $V_1=V_I$} or {$V_1=V_V$, $V_{EX}\,V_I$}
66—Digital control of the analog switch specifying either impedance or admittance mode
67—Threshold detector used to create digital signal $V_0$, which is in phase with $V_{EX}$
68—Phase lock loop used to create digital signal $V_{90}$, which is 90 out of phase from $V_{EX}$
69—Peak detector
70—Four-quadrant mixers, used to mix the two input signals
72—Voltage ($V_{real}$) proportional to the real part of the input signal
74—Voltage ($V_{imag}$) proportional to the imaginary part of the input signal
76—Low power ADC
78—The constant 2 defines the length of the chirp, n=2 means 8 sine waves
80—The software can turn on the analog power by setting P2.6 high
82—Each SinDAC output is synchronized to an ADC input
83—The software can turn off the analog power by clearing P2.6 low
84—Discrete Fourier Transform
86—Phase correction
88—Calculate muscle component
90—Remove muscle component from impedance signal
92—Calculate volume
94—Find the largest volume over the last hour
96—Once an hour output maximum volume using synchronous serial SPI
98—Put the system in deep sleep mode
100—The apparatus includes three parts: the stimulator, the sensor, and the signal processor
110—The apparatus is placed in a housing that provides protection and power
112—The simulator injects voltage or current into the body
114—The sensor measures the response to the stimulation
116—Using either or both the stimulation and sensor response, the signal processor calculates pressure and/or heart volume Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

Literature Cited, all of which are incorporated by reference herein.

1. Bleumink G S, Knetsch A M, Miriam C M, et al. Quantifying the heart failure epidemic: prevalence, incidence rate, lifetime risk and prognosis of heart failure. *European Heart J* 2005, 25, 1614-1619.
2. Moss A, Zareba W, Hall W, et al, for the Multicenter automatic defibrillator implantation trial II. Prophylactic implantation of a defibrillator in patients with myocardial infarction and reduced ejection fraction. *NEJM* 2002, 346, 877-883.
3. Barry G H, Lee K L, Mark D B, et al. Amiodarone or an implantable cardioverter—defibrillator for congestive heart failure. *NEJM* 2005, 35, 225-237.
4. Bristow M R, Saxon L A, Boehmer J, et al. Cardiac-resynchronization therapy with or without an implantable defibrillator in advanced chronic heart failure. *NEJM* 2004, 350, 2140-2150.
5. Cleland J F, Daubert J C, Erdmann E, et al. The effect of resynchronization on morbidity and mortality in heart failure. *NEJM* 2005, 352, 1539-1549.
6. Linde C, Abraham W T, Gold M R, et al. Randomized trial of cardiac resynchronization in mildly symptomatic heart failure patients and in asymptomatic patients with left ventricular dysfunction and previous heart failure symptoms. *JACC* 2008, 52, 1834-1843.
7. Vollmann D, Nägele H, Schauerte P, et al. Clinical utility of intrathoracic impedance monitoring to alert patients with an implanted apparatus of deteriorating chronic heart failure. *Eur Heart J* 2007, 28, 1835-1840.
8. Yu C M, Wang Li, Chau E, et al. Intrathoracic impedance monitoring in patients with heart failure: correlation with fluid status and feasibility of early warning preceding hospitalization. *Circulation* 2005, 112, 841-848.
9. Luthje K, Drescher T, Zenker D, Vollmann D. Detection of heart failure decompensation using intrathoracic impedance monitoring by a triple-chamber implantable defibrillator. *Heart Rhythm* 2005, 2 (9), 997-999.
10. Wang L, Lahtinen S, Lentz L, et al. Feasibility of using an implantable system to measure thoracic congestion in an ambulatory chronic heart failure canine model. *PACE* 2005, 28 (5), 404-411.
11. Magalski A, Adamson P, Gadler F, et al. Continuous ambulatory right heart pressure measurements with an implantable hemodynamic monitor: a multicenter 12-month follow-up study of patients with chronic heart failure. *J Cardiac Failure* 2002, 8: 63-70.
12. Adamson P B, Magalski A, Braunschweig F, et al. Ongoing right ventricular hemodynamics in heart failure. *JACC* 2003, 41, 565-571.
13. Cleland J G, Coletta A P, Freemantle N, et al. *Clinical trials updates from the ACC meeting. European J Heart Failure* 2005, 7: 931-936.
14. Rozenman Y, Schwartz R S, Shah H, Parikh K H. Wireless acoustic communication with a miniature pressure sensor in the pulmonary artery for disease surveillance and therapy of patients with congestive heart failure. *JACC* 2007, 49, 784-789.
15. Abraham W T. Impedance beats weight in predicting heart failure events. *Cardiology News* 2009, 7 (10), 11 (abstract).
16. Ritzema J, Troughton R, Melton I, et al. Physician-directed patient self-management of left atrial pressure in advanced chronic heart failure. *Circulation* 2010, 121, 1086-1095.
17. Stahl C, Beierlein W, Walker T, et al. Intra-cardiac impedance monitors hemodynamic deterioration in a chronic heart failure pig model. *J Cardiovasc Electrophysiol* 2007, 18, 985-990.

18. Stahl C, Walker T, Straub A, et al. Assessing acute ventricular volume changes by intra-cardiac impedance in a chronic heart failure animal model. *PACE* 2009, 32, 1395-1401.
19. Feldman M D, Mao Y, Valvano J W, Pearce J A, Freeman G L. Development of a multifrequency conductance lead-based system to determine LV function in mice. *Am J Physiol, Heart Circ Physiol* 2000, 279, H1411-H1420.
20. Wei C L, Valvano J W, Feldman M D, Pearce J A. Nonlinear conductance-volume relationship for murine conductance lead measurement system. *IEEE Trans Biomedical Engineering* 2005, 52 (10), 1654-1661.
21. Reyes M, Steinhelper M E, Alvarez J A, et al, Feldman M D. Impact of physiologic variables and genetic background on myocardial frequency-resistivity relations in the intact beating murine heart. *Am J Physiol, Heart Circ Physiol* 2006, 291, H1659-H1669.
22. Wei C L, Valvano J W, Feldman M D, Nahrendorf M, Peshock R, Pearce J A. Volume lead parallel conductance varies between end-systole and end-diastole. *IEEE Trans Biomedical Engineering* 2007, 54 (8), 1480-1489.
23. Raghavan K, Porterfield J E, Kottam Anil T, Feldman M D, Escobedo E, Valvano J W, Pearce J A. Electrical conductivity and permittivity of murine myocardium. *IEEE Trans Biomedical Eng*, 2009, 56 (8): 2044-2053.
24. Porterfield J E, Kottam A T, Raghavan K, Escobedo D, Trevino R J, Valvano J W, Pearce J A, Feldman M D. Dynamic correction for parallel conductance, Gp, and gain factor, a, in invasive murine left ventricular volume measurements□. *Journal Applied Physiol*, 2009, 107, 1693-1703.
25. Bann J, Jong T T, Kerkof P, et al. Continuous stroke volume and cardiac output from intraventricular dimensions, obtained with impedance lead. *Cardiovasc Res* 1981, 15, 328-334.
26. Baan J, Van der Velde E T, de Bruin H G, et al. Continuous measurement of left ventricular volume in animals and humans by conductance lead. *Circulation* 1984, 70, 812-823.
27. Stahl C, Beierlein W, Walker T, et al. Intra-cardiac impedance monitors hemodynamic deterioration in a chronic heart failure pig model. *J Cardiovasc Electrophysiol* 2007, 18, 985-990.
28. Stahl C, Walker T, Straub A, et al. Assessing acute ventricular volume changes by intra-cardiac impedance in a chronic heart failure animal model. *PACE* 2009, 32, 1395-1401.
29. Ring and Johnson counters are standard digital circuits. A ring counter is a sequence of flip flops placed in a ring, where the output of each flip-flop is the input to the next. A Johnson counter is a ring counter where one output is complemented before being connected to the next input. http://www.allaboutcircuits.com/vol_4/chpt_12/6.html or http://en.wikipedia.org/wiki/Counter.
30. Agilent Technologies, Agilent Impedance Measurement Handbook, 4th edition, http://cp.literature.agilent.com/litweb/pdf/5950-3000.pdf
31. Porterfield J, Larson E, Jenkins J, Escobedo D, Valvano J, Pearce J, and Feldman M, Left Ventricular Epicardial Admittance Measurement for Detection of Acute LV Dilation, Journal of *Applied Physiology* (JAPPL-01047-2010R1), 2010.
32. Uemura K, Kawada T, Sugimachi M, Zheng C, Kashihara K, Sato T and Sunagawa K 2004 A self-calibrating telemetry system for measurement of ventricular pressure-volume relations in conscious, freely moving rats *Am. J. Physiol. Heart Circ. Physiol.* 287 H2906-H2913
33. Raghavan K, Design of a wireless bio-telemetric apparatus for measurement of left ventricular pressure-volume loops using the admittance technique in conscious, ambulatory rats, PhD dissertation, May 2009.
34. Raghavan K, Feldman M, Porterfield J, Larson E, Jenkins J, Escobedo D, Pearce J, and Valvano J, Bio-telemetric apparatus for measurement of left ventricular pressure-volume loops using the admittance technique in conscious, ambulatory rats, in review, Physiological Measurements.
35. U.S. Patent application 61/459,280.
36. U.S. patent application Ser. No. 12/657,832.
37. U.S. patent application Ser. No. 12/924,195
38. U.S. patent application Ser. No. 12/086,040
39. U.S. patent application Ser. No. 10/568,912
40. U.S. Pat. No. 6,494,832
41. U.S. Pat. No. 6,112,115

The invention claimed is:

1. An apparatus for measuring complex electrical admittance and/or complex electrical impedance in animal or human patients comprising:
    two or more electrodes that are adapted to be disposed in the patient; and
    a housing adapted to be disposed in the patient, the housing having disposed in it a stimulator in electrical communication with two or more electrodes to stimulate with either current or voltage, a sensor in electrical communication with the same stimulating electrodes or with additional electrodes to sense a response based on the stimulation of the stimulating electrodes, the stimulator produces an excitation wave that is any shape that can be defined by a repeated sequence of integer values, whose frequency components range from 0 to 1 mHz, and a signal processor in electrical communication with both the stimulator and the sensor to determine the complex electrical admittance or impedance of the patient, the stimulator produces an excitation wave that is created by a resistor-summing network, called a SinDAC, such that a number of resistors, resistor values, digital output sequence, and rate or digital outputs are selected to define a shape and frequency of the excitation wave.

2. An apparatus described in claim 1 wherein an ADC conversion of the sensor is synchronized to the SinDAC outputs generating the stimulation.

3. An apparatus of claim 2 wherein the SinDAC comprising:
    a microcontroller having a plurality of digital outputs, with each output being either 0 or +V volts; and
    a plurality of resistors forming a resistor-summing network with each digital output connected to one resistor of the plurality of resistors, the resistor-summing network creates a voltage output which is matched to a desired sine wave.

4. An apparatus for measuring complex electrical admittance and/or complex electrical impedance in animal or human patients comprising:
    two or more electrodes that are adapted to be disposed in the patient in communication with a heart of the patient, the two or more electrodes include a stimulating electrode and a sink electrode that are placed on opposite sides of a left ventricle to cause a sensing field to go across a blood pool in the left ventricle: and
    a housing adapted to be disposed in the patient, the housing having disposed in it a stimulator in electrical communication with the two or more electrodes to stimulate with either current or voltage, a sensor in electrical communication with the same stimulating electrode or with additional electrodes to sense a response based on the stimulation of the stimulating electrode, and a signal processor in electrical communication with both the stimulator and the sensor to determine the complex electrical admittance or impedance of the patient, a Discrete Fourier Transform (DFT) is used by the signal processor to extract complex electrical properties to determine heart volume of the heart.

5. An apparatus described in claim 4 wherein the complex measurements occur with an analog circuit using a synchronous demodulator to directly measure either impedance or admittance.

6. An apparatus for measuring complex electrical admittance and/or complex electrical impedance in animal or human patients comprising:

two or more electrodes that are adapted to be disposed in the patient in communication with a heart of the patient, the two or more electrodes include a stimulating electrode and a sink electrode that are placed on opposite sides of a left ventricle to cause a sensing field to go across a blood pool in the left ventricle; and a housing adapted to be disposed in the patient, the housing having disposed in it a stimulator in electrical communication with the two or more electrodes to stimulate with either current or voltage, a sensor in electrical communication with the same stimulating electrodes or with additional electrodes to sense a response based on the stimulation of the stimulating electrode, and a signal processor in electrical communication with both the stimulator and the sensor to determine the complex electrical admittance or impedance of the patient without calculating magnitude and phase in regard to the response to determine heart volume of the heart.

\* \* \* \* \*